US011215702B2

(12) United States Patent
Hyeon

(10) Patent No.: US 11,215,702 B2
(45) Date of Patent: Jan. 4, 2022

(54) ULTRASONIC APPARATUS AND METHOD OF CONTROLLING THE SAME

(71) Applicant: SAMSUNG MEDISON CO., LTD., Gangwon-do (KR)

(72) Inventor: Yongcheol Hyeon, Seoul (KR)

(73) Assignee: SAMSUNG MEDISON CO., LTD., Ganwon-Do (KR)

( * ) Notice: Subject to any disclaimer, the term of this patent is extended or adjusted under 35 U.S.C. 154(b) by 168 days.

(21) Appl. No.: 16/782,596

(22) Filed: Feb. 5, 2020

(65) Prior Publication Data

US 2020/0256969 A1 Aug. 13, 2020

(30) Foreign Application Priority Data

Feb. 8, 2019 (KR) ........................ 10-2019-0014887

(51) Int. Cl.
*G01S 7/52* (2006.01)
*G01S 15/89* (2006.01)
(Continued)

(52) U.S. Cl.
CPC ........ *G01S 7/52004* (2013.01); *A61B 8/4444* (2013.01); *A61B 8/461* (2013.01);
(Continued)

(58) Field of Classification Search
CPC ............... G01S 7/52004; G01S 7/5202; G01S 7/52028; G01S 7/52053; G01S 7/52087;
(Continued)

(56) References Cited

U.S. PATENT DOCUMENTS

2018/0249986 A1 9/2018 Lee et al.
2019/0129021 A1* 5/2019 Heyon ................ G01S 7/52085
2020/0256969 A1* 8/2020 Hyeon .................. G01S 7/5205

FOREIGN PATENT DOCUMENTS

| EP | 3480621 A1 | 5/2019 | |
| EP | 3692924 A1 * | 8/2020 | ......... G01S 7/52053 |
| JP | 4510476 B2 | 7/2010 | |

OTHER PUBLICATIONS

Extended European Search Report dated Jun. 5, 2020 issued in European Patent Application No. 20157260.9.
(Continued)

*Primary Examiner* — Daniel Pihulic
(74) *Attorney, Agent, or Firm* — Morgan, Lewis & Bockius LLP

(57) ABSTRACT

An ultrasonic apparatus including a plurality of channels, each includes a transmission channel configured to generate and output a transmission signal based on a synchronization signal; a transducer element configured to convert the transmission signal output from the transmission channel into an ultrasonic signal and output the ultrasonic signal; a transceiver switching circuit configured to attenuate and output the transmission signal output from the transmission channel, and to output a reception signal that returns after the ultrasonic signal is transmitted to an object and is reflected from the object; and a reception channel configured to receive the attenuated output transmission signal and the output reception signal, and to detect transmission waveform information based on the attenuated transmission signal. The ultrasonic apparatus may further include a controller configured to store reference waveform information according to a transmission condition, and to compare the detected transmission waveform information with the reference waveform information.

8 Claims, 18 Drawing Sheets

(51) Int. Cl.
*A61B 8/08* (2006.01)
*A61B 8/00* (2006.01)
*H04B 1/44* (2006.01)

(52) U.S. Cl.
CPC ............ *A61B 8/5207* (2013.01); *A61B 8/582* (2013.01); *G01S 7/5202* (2013.01); *G01S 7/52028* (2013.01); *G01S 7/52053* (2013.01); *G01S 7/52087* (2013.01); *G01S 15/8925* (2013.01); *H04B 1/44* (2013.01)

(58) Field of Classification Search
CPC ............ G01S 15/8925; G01S 7/52077; G01S 7/5205; A61B 8/4444; A61B 8/461; A61B 8/5207; A61B 8/582; A61B 8/54; A61B 8/58; A61B 8/4477; H04B 1/44; B06B 2201/40; B06B 1/0215
See application file for complete search history.

(56) References Cited

OTHER PUBLICATIONS

European Communication dated Mar. 29, 2021 issued in European Patent Application No. 20157260.9.

* cited by examiner

FIG. 12
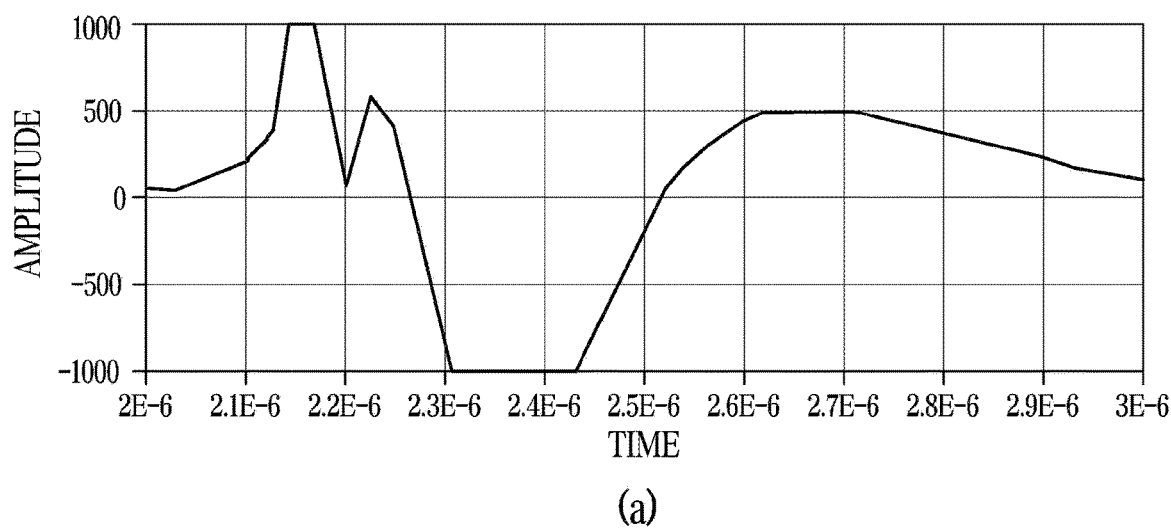
(a)
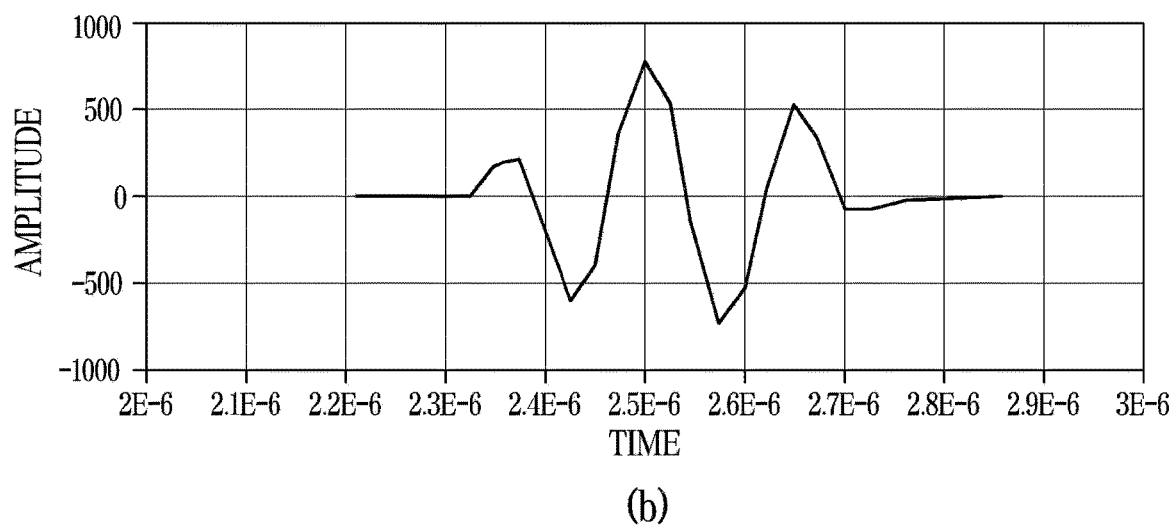
(b)

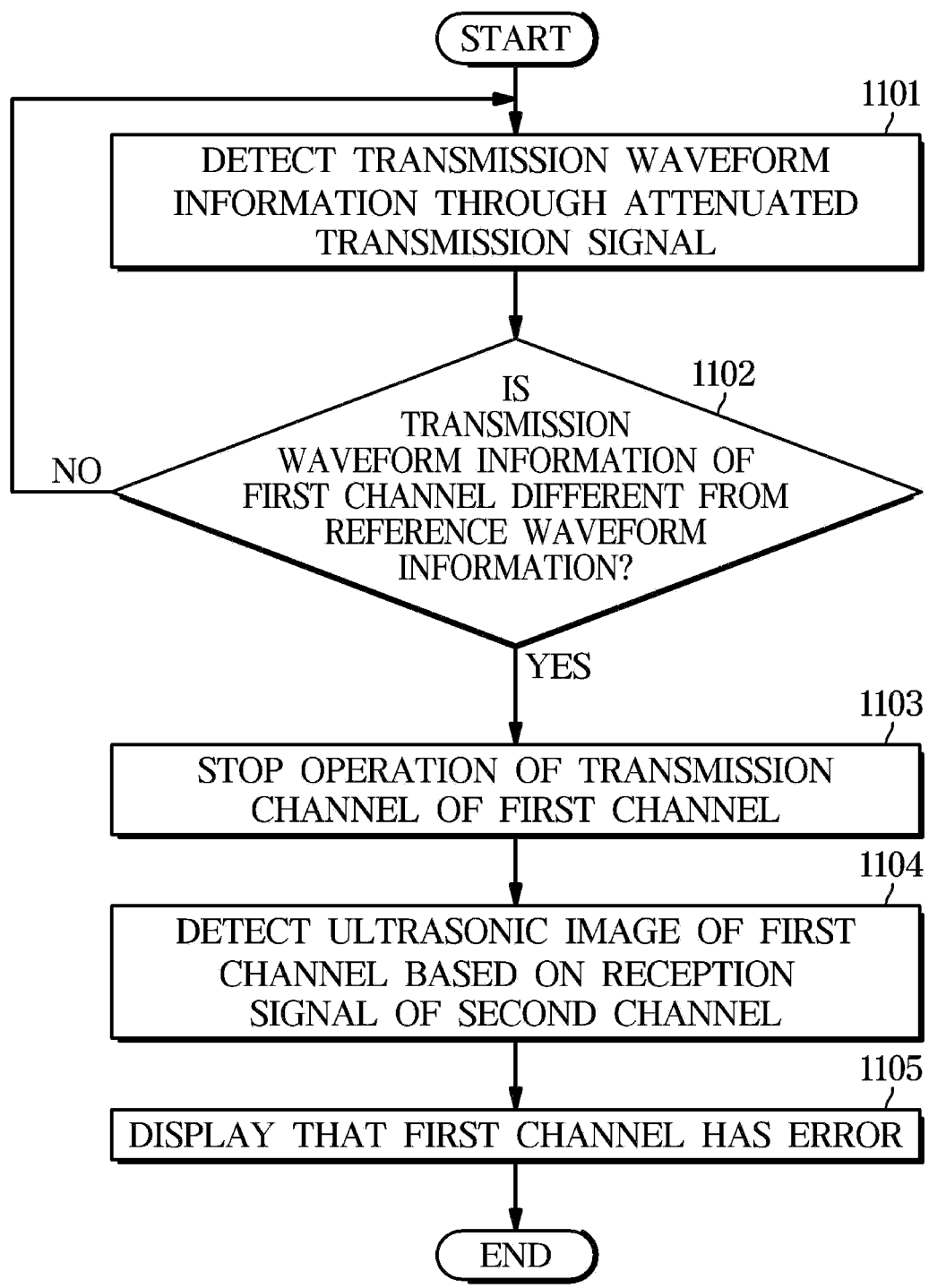

ULTRASONIC APPARATUS AND METHOD OF CONTROLLING THE SAME

CROSS-REFERENCE TO RELATED APPLICATION(S)

This application is based on and claims priority under 35 U.S.C. § 119 to Korean Patent Application No. 10-2019-0014887, filed on Feb. 8, 2019 in the Korean Intellectual Property Office, the disclosure of which is incorporated by reference in its entirety.

TECHNICAL FIELD

The disclosure relates to an ultrasonic apparatus for determining whether the ultrasonic apparatus is normally operated by detecting waveforms of transmission signals generated from the ultrasonic apparatus in real time, and a method of controlling the ultrasonic apparatus.

BACKGROUND

An ultrasonic apparatus operates to irradiate an ultrasonic signal generated from an ultrasonic probe transducer to a target portion inside an object through the surface of the object and receive an ultrasonic signal (ultrasonic echo signal) reflected from the object to obtain an image of the internal state of the object.

The ultrasonic apparatus has advantages in that it is compact and inexpensive, is displayable in real time, and has high safety compared to an X-ray imaging apparatus due to having no risk of exposure to X-rays or the like, and thus are widely used in a variety of fields, such as medical fields and the like.

SUMMARY

Therefore, it is an aspect of the disclosure to provide an ultrasonic apparatus for correcting deformation of an ultrasonic image due to an abnormality of a transmission circuit by detecting transmission waveforms in real time without an additional reception channel in detecting waveforms of transmission signals output by the ultrasonic apparatus in real time, and a method of controlling the ultrasonic apparatus.

Additional aspects of the disclosure will be set forth in part in the description which follows and, in part, will be obvious from the description, or may be learned by practice of the disclosure.

In accordance with an aspect of the disclosure, an ultrasonic apparatus including a plurality of channels, each includes a transmission channel configured to generate and output a transmission signal based on a synchronization signal; a transducer element configured to convert the transmission signal output from the transmission channel into an ultrasonic signal and output the ultrasonic signal; a transceiver switching circuit configured to attenuate and output the transmission signal output from the transmission channel, and to output a reception signal that returns after the ultrasonic signal is transmitted to an object and is reflected from the object; and a reception channel configured to receive the attenuated output transmission signal and the output reception signal, and to detect transmission waveform information based on the attenuated transmission signal. The ultrasonic apparatus may further include a controller configured to store reference waveform information according to a transmission condition, and to compare the detected transmission waveform information with the reference waveform information.

When the detected transmission waveform information is different from the reference waveform information, the controller may be configured to stop an operation of the transmission channel.

The plurality of channels may include a first channel and a second channel including a transducer element adjacent to a transducer element of the first channel. The controller may be configured to, when the transmission waveform information detected in the first channel is different from the reference waveform information, stop the operation of the transmission channel of the first channel; and control the reception channel of the first channel such that a reception channel of the first channel obtains an ultrasonic image data based on a reception signal received by a reception channel of the second channel.

The ultrasonic apparatus may further include a display. When the detected transmission waveform information is different from the reference waveform information, the controller may be configured to display that there is an error in the transmission channel through the display.

In accordance with another aspect of the disclosure, a method of controlling an ultrasonic apparatus including a plurality of channels, the method includes generating and outputting, by a transmission channel, a transmission signal based on a synchronization signal; converting, by a transducer element, the transmission signal into an ultrasonic signal, and outputting, by a transceiver switching circuit, a reception signal that returns after the ultrasonic signal is transmitted to an object and is reflected from the object; attenuating and outputting, by the transceiver switching circuit, the transmission signal; receiving, by a reception channel, the attenuated output transmission signal and the output reception signal, and detecting transmission waveform information based on the attenuated transmission signal; and comparing, by a controller, the detected transmission waveform information with reference waveform information.

The method may further include, when the detected transmission waveform information is different from the reference waveform information, stopping, by the controller, an operation of the transmission channel.

The plurality of channels may include a first channel and a second channel including a transducer element adjacent to a transducer element of the first channel. The method may further include, when the transmission waveform information detected in the first channel is different from the reference waveform information, stopping, by the controller, the operation of the transmission channel of the first channel; and controlling, by the controller, the reception channel of the first channel such that a reception channel of the first channel detects an ultrasonic image based on a reception signal received by a reception channel of the second channel.

The method may further include, when the detected transmission waveform information is different from the reference waveform information, displaying, by the controller, that there is an error in the transmission channel.

BRIEF DESCRIPTION OF THE DRAWINGS

These and/or other aspects of the disclosure will become apparent and more readily appreciated from the following description of the embodiments, taken in conjunction with the accompanying drawings of which:

FIG. 12 is a graph illustrating a transmission waveform according to exemplary embodiments of the disclosure;

FIG. 17 is a flowchart illustrating a method of controlling an ultrasonic apparatus according to another embodiment.

DETAILED DESCRIPTION

Figure 1:
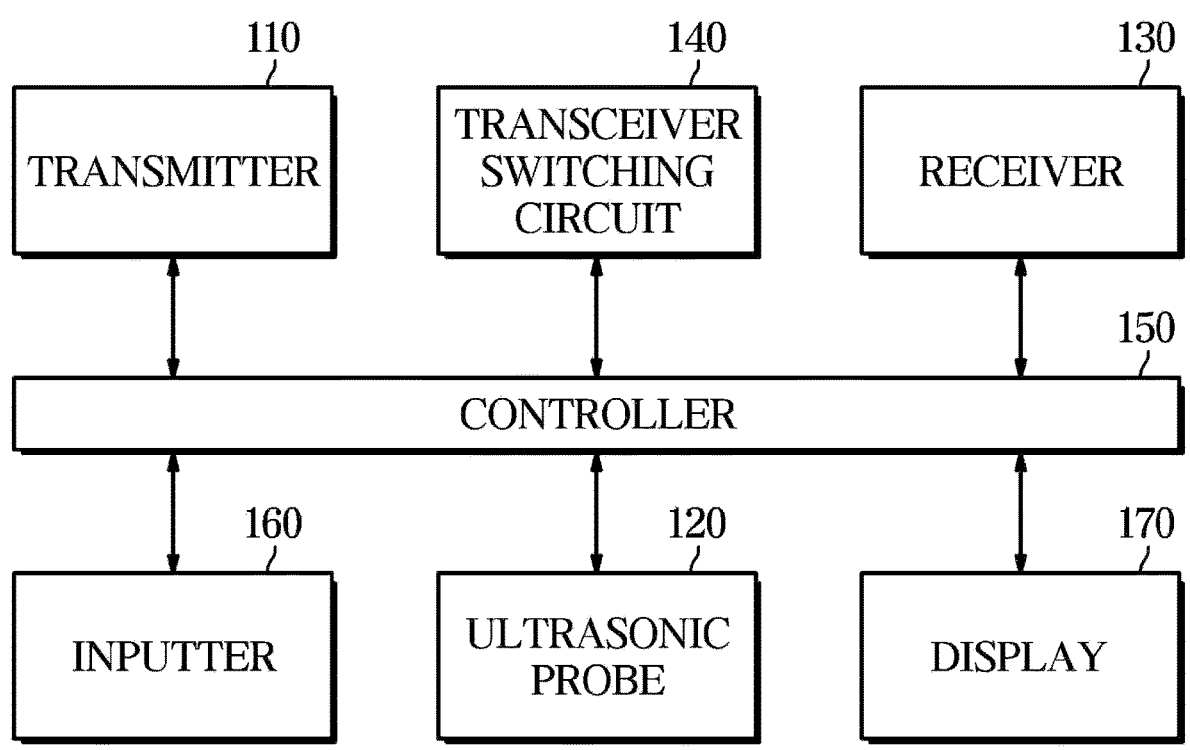
FIG. 1 is a control block diagram of an ultrasonic apparatus according to exemplary embodiments of the disclosure.

Like reference numerals refer to like elements throughout the specification. Not all elements of exemplary embodiments of the disclosure will be described, and description of what are commonly known in the art or what overlap each other in the embodiments will be omitted. The terms as used throughout the specification, such as "~part," "~module," "~member," "~block," etc., may be implemented in software and/or hardware, and a plurality of "~parts," "~modules," "~members," or "~blocks" may be implemented in a single element, or a single "~part," "~module," "~member," or "~block" may include a plurality of elements.

It will be understood that when an element is referred to as being "connected" to another element, it can be directly or indirectly connected to the other element, wherein the indirect connection includes "connection" via a wireless communication network.

When a part "includes" or "comprises" an element, unless there is a particular description contrary thereto, the part may further include other elements, not excluding the other elements.

Further, it will be further understood when a signal or data is transferred, sent or transmitted from "an element" to "another element", it does not exclude another element between the element and the other element passed by the signal or data therethrough, unless the context clearly indicates otherwise.

It will be understood that, although the terms first, second, third, etc., may be used herein to describe various elements, it should not be limited by these terms. These terms are only used to distinguish one element from another element.

As used herein, the singular forms "a," "an" and "the" are intended to include the plural forms as well, unless the context clearly indicates otherwise.

An identification code is used for the convenience of the description but is not intended to illustrate the order of each step. Each of the steps may be implemented in an order different from the illustrated order unless the context clearly indicates otherwise.

Hereinafter, exemplary embodiments of an ultrasonic apparatus according to an aspect and a method of controlling the ultrasonic apparatus will be described with reference to the accompanying drawings in detail.

Figure 2:
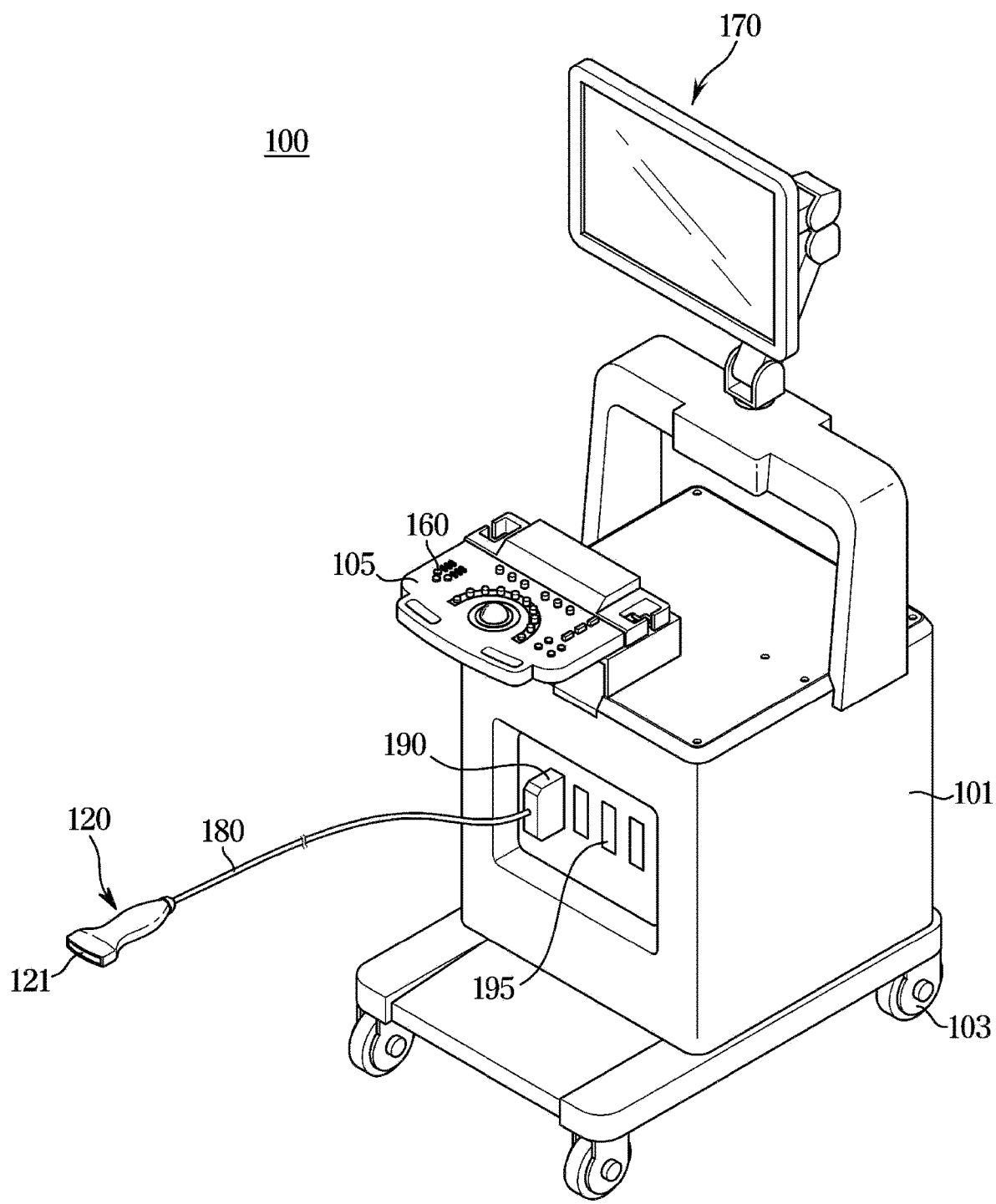
FIG. 2 is a view illustrating an exterior of an ultrasonic apparatus according to exemplary embodiments of the disclosure.

FIG. 1 is a control block diagram of an ultrasonic apparatus according to exemplary embodiments of the disclosure, and FIG. 2 is a view illustrating an exterior of an ultrasonic apparatus according to exemplary embodiments of the disclosure.

Referring to FIGS. 1 and 2, an ultrasonic apparatus 100 may include a transmitter 110 for outputting a transmission signal converted into an ultrasonic signal by an ultrasonic probe 120, the ultrasonic probe 120 for transmitting the ultrasonic signal to an object, receiving an ultrasonic echo signal reflected from the object, and outputting a reception signal based on the ultrasonic echo signal, a transceiver switching circuit 140 for attenuating and passing the transmission signal and passing the reception signal passes without attenuation, a receiver 130 for receiving the reception signal and the attenuated transmission signal, a controller 150 for controlling operations of internal components of the ultrasonic apparatus 100, an inputter 160, and a display 170.

The transmitter 110 may output the transmission signal for obtaining a frame of an ultrasonic image. The transmission signal output by the transmitter 110 may correspond to an electrical signal. Frames of the ultrasonic images may include an amplitude mode (A-mode) frame, a brightness mode (B-mode) frame, a color mode (C-mode) frame, a doppler mode (D-mode) frame, an elastography mode (E-mode) frame, a motion mode (M-mode) frame, and a frame of an elastography image.

In detail, the transmitter 110 may output the transmission signal according to a control signal of the controller 150. The transmitter 110 may output the transmission signal with a time delay set on the basis of a synchronization signal having a pulse repetition frequency (PRF). Accordingly, the transmission signal generated by the transmitter 110 may be a pulse having a repetition frequency.

The transmitter 110 including a plurality of transmission channels 210-1, 210-2, . . . , and 210-N may output a plurality of transmission signals. In detail, the transmitter 110 may include the plurality of transmission channels 210-1, 210-2, . . . , and 210-N each connected to a corresponding one of a plurality of transducer elements 121-1, 121-2, . . . , and 121-N of the ultrasonic probe 120, and transmits a plurality of transmission signals to the plurality of transducer elements 121-1, 121-2, . . . , and 121-N through each of the transmission channels 210-1, 210-2, . . . , and 210-N.

The transmission signals of the transmitter 110 may generally correspond to high voltage signals. In detail, the transmission signal may have a voltage of 200 Vp-p at the maximum. The reception signals output by ultrasonic probe 120 on the basis of the ultrasonic echo signal reflected from the object correspond to low voltage signals compared to the transmission signals of the transmitter 110. Therefore, in general, the receiver 130 of the ultrasonic apparatus 100 may use a range corresponding to a voltage of the reception signal of the ultrasonic probe 120 as an input range.

The ultrasonic probe 120 may be a part that comes into a contact with the body surface of the object or is inserted into the body of the object, and may transmit and receive ultrasonic. In detail, the ultrasonic probe 120, upon receiving the transmission signal transmitted from the transmitter 110, may convert the transmission signal into the ultrasonic signal, transmit ultrasonic into the object, receive the ultrasonic echo signal reflected from a specific portion inside the object, convert the ultrasonic echo signal into a reception signal in the form of an electrical signal, and transmit the ultrasonic echo signal to the receiver 120.

To this end, the ultrasonic probe 120 may include the plurality of transducer elements 121 and a multiplexer (MUX) circuit. The plurality of transducer elements 121 may include a plurality of elements that may vibrate to convert the electrical signal into ultrasonic or convert ultrasonic into the electrical signal. The plurality of transducer elements 121 may be arranged on one surface of a housing of the ultrasonic probe. In detail, the plurality of transducer elements 121 may be arranged in a direction parallel to an opening provided on the one surface of the housing such that ultrasonic transmission and reception may be performed through the opening. The ultrasonic probe 120 may convert the transmission signal into the ultrasonic signal or convert the ultrasonic echo signal into the reception signal using the plurality of transducer elements 121.

The plurality of transducer elements 121 of the ultrasonic probe 120 may be implemented as piezoelectric transducers using piezoelectric effects. To this end, the transducer elements 121 may include a piezoelectric material or a piezoelectric thin film. When alternating current is applied to the piezoelectric material or piezoelectric thin film from an internal charging device, such as a battery, or an external power supply device, the piezoelectric material or piezoelectric thin film vibrate with a predetermined frequency according to the applied alternating current and ultrasonic waves of the predetermined frequency are generated according to the vibration frequency.

On the other hand, when ultrasonic echo waves of the predetermined frequency reach the piezoelectric material or piezoelectric thin film, the piezoelectric material or piezoelectric thin film vibrates according to the ultrasonic echo waves. In this regard, the piezoelectric material or piezoelectric thin film outputs alternating current of a frequency corresponding to the vibration frequency thereof.

In addition, the transducer elements 121 of the ultrasonic probe 120 may be implemented as other types of transducer elements, such as a magnetostrictive ultrasonic transducer using the magnetostrictive effect of a magnetic material, or a capacitive micromachining ultrasonic transducer (cMUT) that transmits and receives ultrasonic waves using vibrations of several hundreds or thousands of micromachined thin films.

Each of the plurality of transducer elements 121-1, 121-2, . . . , and 121-N of the ultrasonic probe 120 may be connected to a corresponding one of the plurality of transmission channels 210-1, 210-2, . . . , and 210-N of the transmitter 110 to receive the transmission signal output by the transmitter 210. Each of the plurality of transducer elements 121 of the ultrasonic probe 120 may be also connected to a correspond one of a plurality of reception channels 130-1, 130-2, . . . , and 130-N of the receiver 130 to transmit the reception signal to the receiver 130.

The ultrasonic probe 120 may be connected to a main body 101 through a cable 180 or by using a wireless communication network to receive various signals required for controlling the ultrasonic probe 120 from the transmitter 110 embedded in the main body 101. The reception signal corresponding to the ultrasonic echo signal received or received by the ultrasonic probe 120 may be transmitted to the receiver 130 embedded in the main body 101.

The receiver 130 may detect the ultrasonic image by receiving the reception signal output from the ultrasonic probe 120. In detail, the receiver 130 may include an amplifier for amplifying an input signal, an analog-to-digital converter (ADC) for converting the input signal into a digital signal, and a digital signal processor. The receiver 130 may detect the ultrasonic image by amplifying the reception signal, converting the reception signal into the digital signal, and processing the reception signal.

Particularly, each of the plurality of reception channels 130-1, 130-2, . . . , and 130-N may include the amplifier for amplifying the input signal, the ADC for converting the input signal into the digital signal, and the digital signal processor, respectively. That is, the receiver 130 may convert the plurality of reception signals received through the plurality of reception channels 130-1, 130-2, . . . , 130-N to the digital signal, receive and focus a plurality of digitally converted reception signals, and detect a plurality of ultrasonic images using a plurality of reception focused signals.

As such, since the receiver 130 is intended to receive and process the reception signal output from the ultrasonic probe 120, a voltage input range of the receiver 130 may use a voltage range of the reception signal. Therefore, the receiver 130 has difficulty in receiving a high voltage transmission signal output from the transmitter 110 without distortion. In addition, when receiving the high voltage transmission signal exceeding the input range of the receiver 130, the receiver 130 may be damaged. Accordingly, in a conventional ultrasonic apparatus, a switch is disposed between the transmitter and the receiver to block the transmission of the high voltage transmission signal output from the transmitter to the receiver, thereby minimizing the transmission of the transmission signal to the receiver.

The transceiver switching circuit 140 may include a conventional switch as it is, but add a resistor to attenuate the transmission signal output from the transmitter 110 and transmit it to the receiver 130. The transceiver switching circuit 140 may attenuate the transmission signal output from the transmitter 110 to the receiver 130, and transmit the reception signal output from the ultrasonic probe 120 to the receiver 130 without attenuation. Since the transmission signal is attenuated and delivered to the receiver 130, the receiver 130 may receive the transmission signal without distortion and may solve the error of the receiver 130 being broken.

The transceiver switching circuit 140 may be connected to each of the plurality of transmission channels 110-1, 110-2, . . ., and 110-N to attenuate the transmission signal output from each of the plurality of transmission channels 110-1, 110-2, . . ., and 110-N and transmit the attenuated signal to each of the plurality of reception channels 130-1, 130-2, . . ., and 130-N. That is, the transceiver switching circuit 140-1, 140-2, . . ., and 140-N may be provided for each channel.

In detail, the transceiver switching circuit 140 may attenuate the transmission signal received from the transmitter 110 and transmit the attenuated transmission signal to the receiver 130 in the transmission section in which the transmitter 110 outputs the transmission signal. The transmission signal may be attenuated so as not to exceed the input range of the receiver 130.

In addition, the transceiver switching circuit 140 may transmit the reception signal received from the ultrasonic probe 120 to the receiver 130 without attenuation in the reception section in which the ultrasonic probe 120 outputs the reception signal. As such, since the receiver 130 may receive the reception signal without attenuation, there is no problem in the reception performance of the ultrasonic apparatus 100.

The transceiver switching circuit 140 may include a switching module operative to block the transmission signal from being transmitted to the receiver 130 and to transmit the reception signal to the receiver 130 and the resistor for attenuating the transmission signal.

The transceiver switching circuit 140 may operate to deactivate the switching module in the transmission section in which the transmitter 110 outputs the transmission signal so that the transmission signal is attenuated through the resistor and transmitted to the receiver 130, and may operate to activate the switching module in the reception section in which the ultrasonic probe 120 outputs the reception signal so that the reception signal is transmitted to the receiver 130 without attenuation through the switching module.

By operation of the transceiver switching circuit 140 described above, the receiver 130 may receive the attenuated transmission signal and non-attenuated reception signals.

In addition, the receiver 130 may detect transmission waveform information based on the attenuated transmission signal. The transmission waveform information may be information about the waveform of the transmission signal output from the transmitter 110, and may include at least one of information about the waveform of the transmission signal, an amplitude of the transmission signal, and a generation time of the transmission signal based on the synchronization signal.

The controller 150 may control the operation of the internal components of the ultrasonic apparatus 100. Particularly, the controller 150 may control the transmitter 110 to output the transmission signal according to a transmission condition, and may control the ultrasonic probe 120 to output the reception signal based on the transmission signal.

In addition, the controller 150 may control the transceiver switching circuit 140 to activate or deactivate the switching module between the transmission section in which the transmission signal is output and the reception section in which the reception signal is output, and may control the receiver 130 to receive the reception signal and the attenuated transmission signal.

The controller 150 may control the display 170 to display the ultrasonic image obtained based on the reception signal and the transmission waveform information obtained based on the transmission signal and notify the user, and may receive and store the transmission condition from the user through the inputter 160.

The controller 150 may store a plurality of reference waveform information corresponding to each of the plurality of transmission conditions, and may compare the detected transmission waveform information with reference waveform information corresponding to the same transmission condition.

The controller 150 may continuously identify whether the ultrasonic apparatus 100 operates normally based on the comparison result. When the comparison result is different, the controller 150 may control the display 170 to notify the user that there is an error and may stop the ultrasonic apparatus 100.

In addition, when the comparison result is different, the controller 150 may correct the transmission signal corresponding to the detected transmission waveform information. In detail, the controller 150 may control the transmitter 110 to allow the transmitter 110 to output the transmission signal having the same waveform as the reference waveform corresponding to the transmission condition. The transmitter 110 may correct the transmission signal such that the transmission signal has the same waveform as the reference waveform corresponding to the transmission condition by adjusting a voltage gain of the transmission signal or an output delay time based on the control of the controller 150.

The controller 150 may compare the transmission waveform information corresponding to the corrected transmission signal with reference waveform information. When the comparison result is different, the controller 150 may control the display 170 to notify the user that there is the error and may stop the ultrasonic apparatus 100.

The inputter 160 may receive a command for starting a diagnosis, selecting a diagnosis portion, selecting a diagnosis type, selecting a mode for the ultrasonic image, and the like from the user. Particularly, the inputter 160 may receive the transmission condition for the transmission signal output from the transmitter 110 from the user, and may transmit the transmission condition to the transmitter 110 through the controller 150.

The transmission condition may vary according to the diagnosis portion, the diagnosis type, the mode for the ultrasonic image, and the like, and generally include an amplitude magnitude of the transmission signal, a frequency, and the generation time of the transmission signal based on the synchronization signal.

The display 170 may display the ultrasonic image and the transmission waveform information according to the control signal of the controller 150. In addition, the display 170 may notify the user that the ultrasonic apparatus 100 is the error according to the comparison result of the transmission waveform information and the reference waveform information. The display 170 may simultaneously display the ultrasonic image and the transmission waveform information, and may display only the ultrasonic image or the transmission waveform information according to the user's selection.

As illustrated in FIG. 2, the ultrasonic apparatus 100 according to the embodiment may include the ultrasonic probe 120 for transmitting the ultrasonic signal to the object, receiving the ultrasonic echo signal reflected from the object, and converting the ultrasonic echo signal into the electrical signal, the main body 101, and the inputter 160, and the display 170.

The ultrasonic probe 120 may be connected to the main body 101 through the cable 180 to receive various signals required for controlling the ultrasonic probe 120 or transmit a reception signal corresponding to the ultrasonic echo signals received by the ultrasonic probe 120.

The reception signal may be one of an analogue signal and a digital signal into which the ultrasonic echo signal has been electrically converted by the ultrasonic probe 120.

The main body 101 may be provided at one side thereof with one or more female connectors 195. A male connector 190 provided at one end of the cable 180 may be physically coupled to the female connector 195.

However, the embodiment of the ultrasonic probe 120 is not limited thereto, and the ultrasonic probe 120 may be wirelessly connected to the main body 101. In this case, the ultrasonic probe 120 may be implemented as a wireless probe to transmit and receive signals through a network formed between the ultrasonic probe 120 and the main body 101. In addition, a plurality of the ultrasonic probes 120 may be connected to a single main body 101.

The main body 101 may be provided at a lower portion with a plurality of casters 103 for the movement of the ultrasonic apparatus 100. The user may fix or move the ultrasonic apparatus 100 using the plurality of casters 103. The ultrasonic apparatus 100 may be referred to as a cart-type ultrasonic apparatus 100.

The main body 101 may be provided at a front surface with an operation panel 105. The inputter 160 for receiving a user's input may be formed on the operation panel 105, and allows a user to input commands for starting the diagnosis, selecting the diagnosis portion, selecting the diagnosis type, selecting the mode for ultrasonic image through the input 160.

The display 170 may be provided at an upper side of the main body 101. The display 170 may be implemented as at least one of various display panels, such as a liquid crystal display (LCD) panel, a light emitting diode (LED) panel, or an organic light emitting diode (OLED) panel.

In addition, the display 170 may be composed of two or more displays such that each display simultaneously displays a different image. For example, one display may display a two-dimensional (2D) ultrasonic image, and the other display may display a three-dimensional (3D) ultrasonic image. Alternatively, one display may display a B-mode image, and the other display may display a contrast agent image. Alternatively, one display may display an ultrasonic image, and the other display may display a temperature information signal of a transmission channel.

The display 170 may display the ultrasonic image on the basis of the reception signal received from the ultrasonic probe 120, and may display waveform information of the transmission signal based on the transmission signal.

The user, such as a doctor, may diagnose a specific disease using the ultrasonic image displayed on the display 170, and the site for obtaining the ultrasonic image may vary according to a diagnosis target disease.

In addition, the user, such as the doctor, may determine whether the ultrasonic apparatus 100 is normally operated using the waveform information of the transmission signal displayed on the display 170. With such a configuration, the patient may be protected from abnormal operation during use of the ultrasonic apparatus 100 and the probability of misdiagnosis may be reduced.

One or more probe holders for mounting the ultrasonic probe 120 may be provided on an outer circumferential surface of the main body 101. Accordingly, when the user does not use the ultrasonic probe 120, the user may store the ultrasonic probe 120 on the probe holder.

The main body 101 may include the transmitter 110, the receiver 130, the transceiver switching circuit 140, and the controller 150. The transmitter 110, the receiver 130, the transceiver switching circuit 140, and the controller 150 may include at least one memory in which a program for performing operations of the ultrasonic apparatus 100 is stored and at least one processor for executing the stored program. The transmitter 110, the receiver 130, the transceiver switching circuit 140, and the controller 150 may use separate memories and separate processors, or may share a memory and a processor.

On the other hand, the appearance of the ultrasonic apparatus 100 according to the embodiment is not limited to the example illustrated in FIG. 2. For example, the ultrasonic apparatus 100 may be implemented in a portable type. When the ultrasonic apparatus 100 is implemented as a portable type, the main body 101 may be provided in the form of a laptop computer, a personal digital assistant (PDA), a tablet personal computer (PC), and the like, and when connected to the ultrasonic probe 120, may generates an ultrasonic image.

Figure 3:
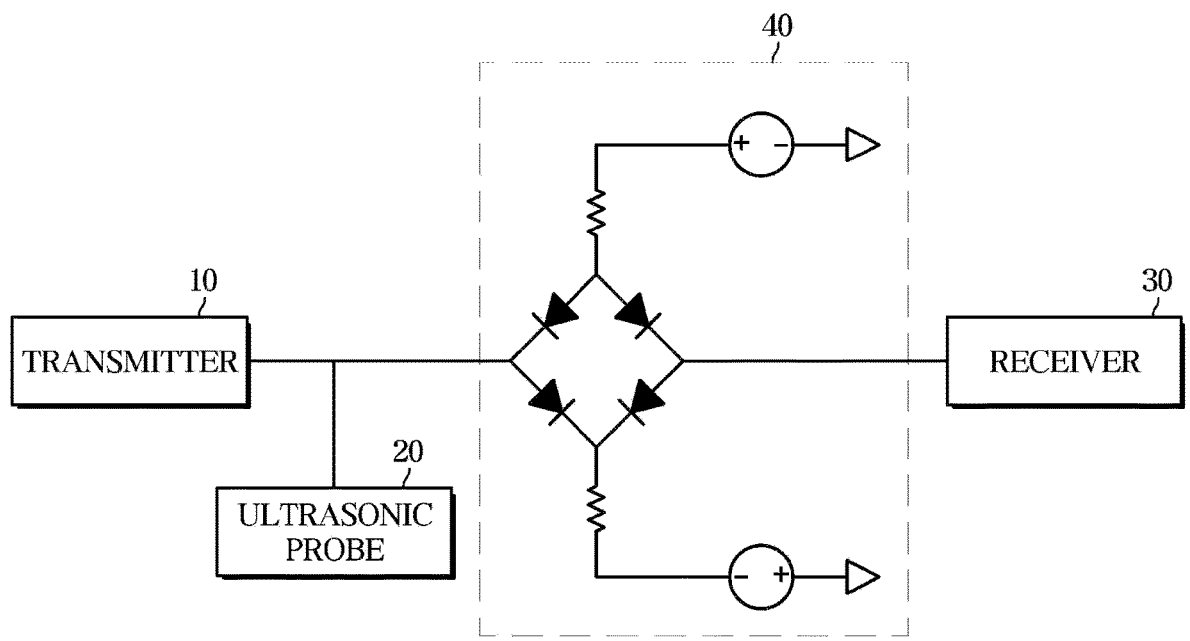
FIG. 3 is a circuit diagram of a conventional ultrasonic apparatus.
Figure 4:
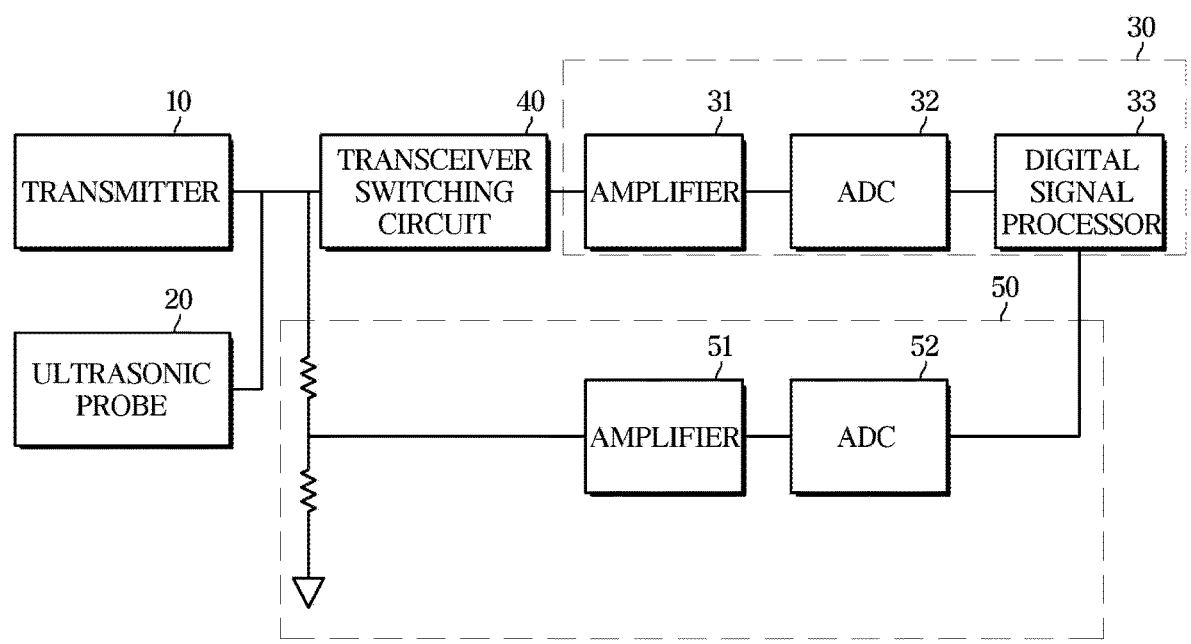
FIG. 4 is a block diagram of an ultrasonic apparatus for obtaining a conventional transmission waveform.

FIG. 3 is a circuit diagram of a conventional ultrasonic apparatus, and FIG. 4 is a block diagram of an ultrasonic apparatus for obtaining a conventional transmission waveform.

Referring to FIGS. 3 and 4, the conventional ultrasonic apparatus may include a transmitter 10 for outputting the transmission signal converted into the ultrasonic signal, an ultrasonic probe 20 for transmitting the ultrasonic signal to the object, and converting and outputting the ultrasonic echo signal reflected from the object to the reception signal, an amplifier 31, an ADC 32, and a digital signal processor 33, and may include a receiver 30 for receiving the reception signal and obtaining the ultrasonic image and a transceiver switching circuit 40 for blocking the transmission signal and passing the reception signal.

The transceiver switching circuit 40 of the conventional ultrasonic apparatus may block the transmission signal output from the transmitter 10 from being received to the receiver 30. In detail, the transceiver switching circuit 40 may transmit a high voltage transmission signal output from the transmitter 10 to the ultrasonic probe 20 by connecting connect the transmitter 10 and the ultrasonic probe 20 in a transmission section in which the transmitter 10 outputs the transmission signal. At the same time, the transceiver switching circuit 40 may completely isolate the receiver 30 from the high voltage transmission signal.

In addition, the transceiver switching circuit 40 may connect the ultrasonic probe 20 and the receiver 30 in the reception section in which the ultrasonic probe 20 outputs the reception signal to transmit the reception signal provided from the ultrasonic probe 20 to the receiver 30.

The transceiver switching circuit 40 may include a diode bridge that is switchable between a first state and a second state. The transceiver switching circuit 40 may apply a reverse bias current to the diode bridge in the first state to block transmission of the transmission signal to the receiver 30, and may operate a forward bias current to the diode bridge in the second state so that the reception is transmitted to the receiver 30.

As such, the conventional ultrasonic apparatus may block transmission of the transmission signal output from the transmitter 10 to the receiver 30. The transceiver switching circuit 40 of the conventional ultrasonic apparatus may block the transmission signal from being transmitted to the receiver 30 so that the high voltage transmission signal output from the transmitter 10 does not damage the receiver 30 that processes only the low voltage signal. The transceiver switching circuit 40 may operate to transmit only the low voltage reception signal reflected from a human body to the receiver 30.

Therefore, the conventional ultrasonic apparatus cannot identify the waveform of the transmission signal in real time using the receiver 30, and requires a separate receiving circuit having the same number of attenuation circuits and ADCs as the number of transmission channels of the transmitter 10.

Referring to FIG. 4, in order to identify the waveform of the transmission signal, the conventional ultrasonic apparatus may divide the voltage of the transmission signal into the resistor at output terminals of all the transmission channels of the transmitter 10 to lower the voltage level, and then convert the transmission signal into the digital signal using an amplifier 51 and a ADC 52.

As such, in order for the conventional ultrasonic apparatus to identify the waveform of the transmission signal, the conventional ultrasonic apparatus should be provided a separate receiving circuit 50 including the amplifier 51 and the ADC 52 for each transmission channel in addition to the amplifier 31 and the ADC 32 on the conventional receiver 30. Providing the additional amplifier 51 and an ADC 52 for each transmission channel has an error in that the reception channel is doubled to increase a size of the circuit.

In addition to providing the additional amplifier 51 and ADC 52 for each transmission channel, providing one amplifier and ADC connected to all transmission channels, it is impossible to detect the waveform of the transmission signal in real time because only one transmission channel must be activated in order to detect the waveform of the transmission signal. Further, it may be used only for the purpose of determining whether a pulser of each transmission channel is operating normally for manufacturing or service purposes.

In addition, when a circuit capable of detecting the waveform of the transmission signal is not provided inside the ultrasonic apparatus, the ultrasonic apparatus should use a separate measuring equipment outside the ultrasonic apparatus.

Figure 5:
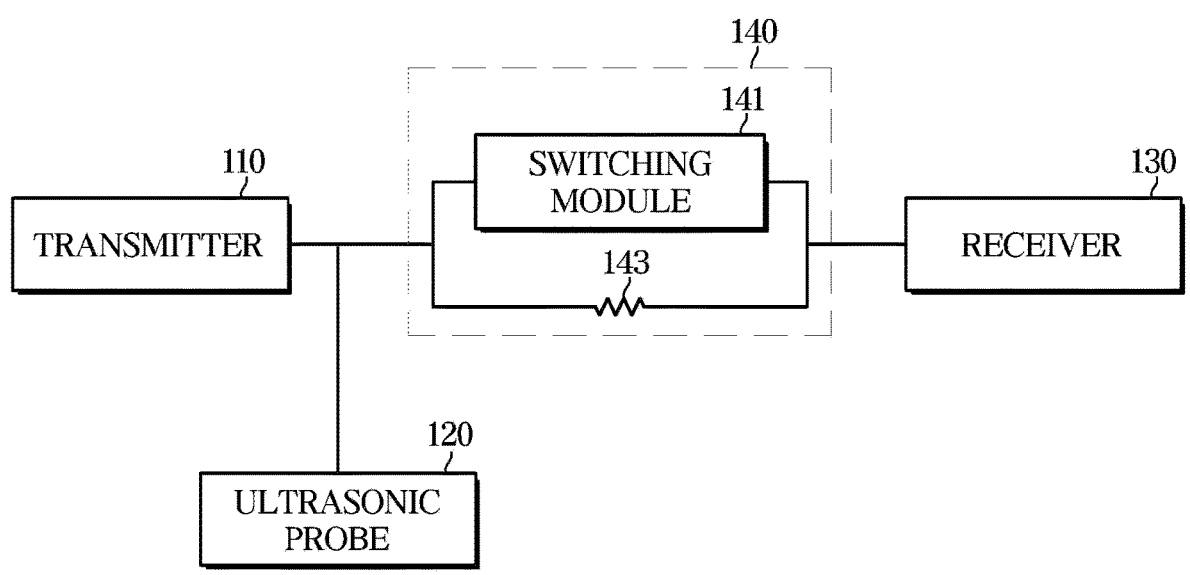
FIG. 5 is a block diagram of an ultrasonic apparatus according to exemplary embodiments of the disclosure.
Figure 6:
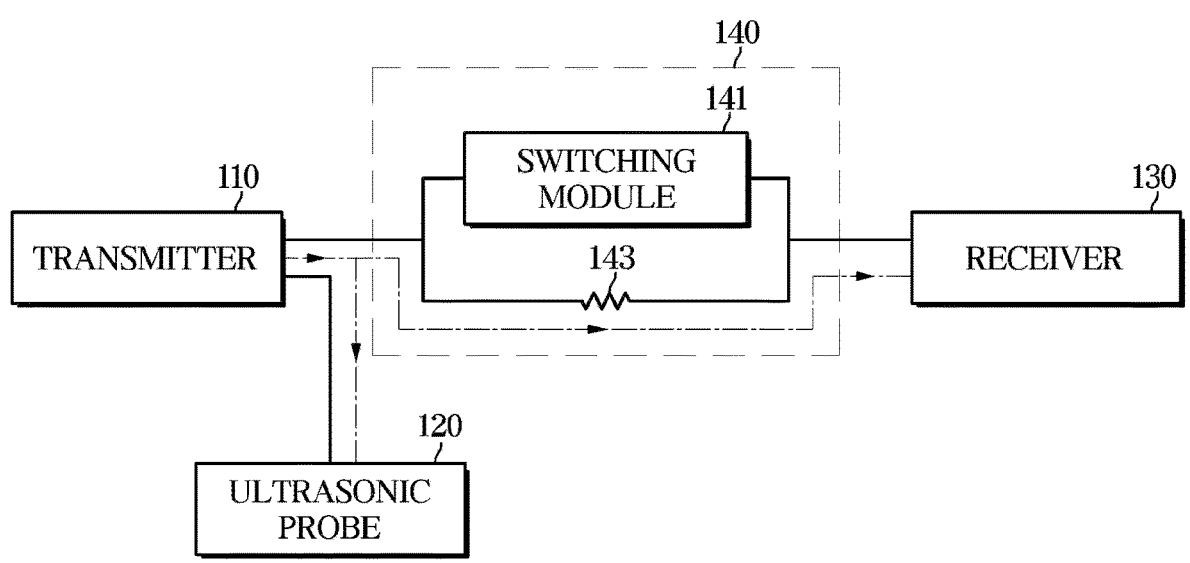
FIG. 6 is a view for describing a flow of a transmission signal in a transmission section according to exemplary embodiments of the disclosure.
Figure 7:
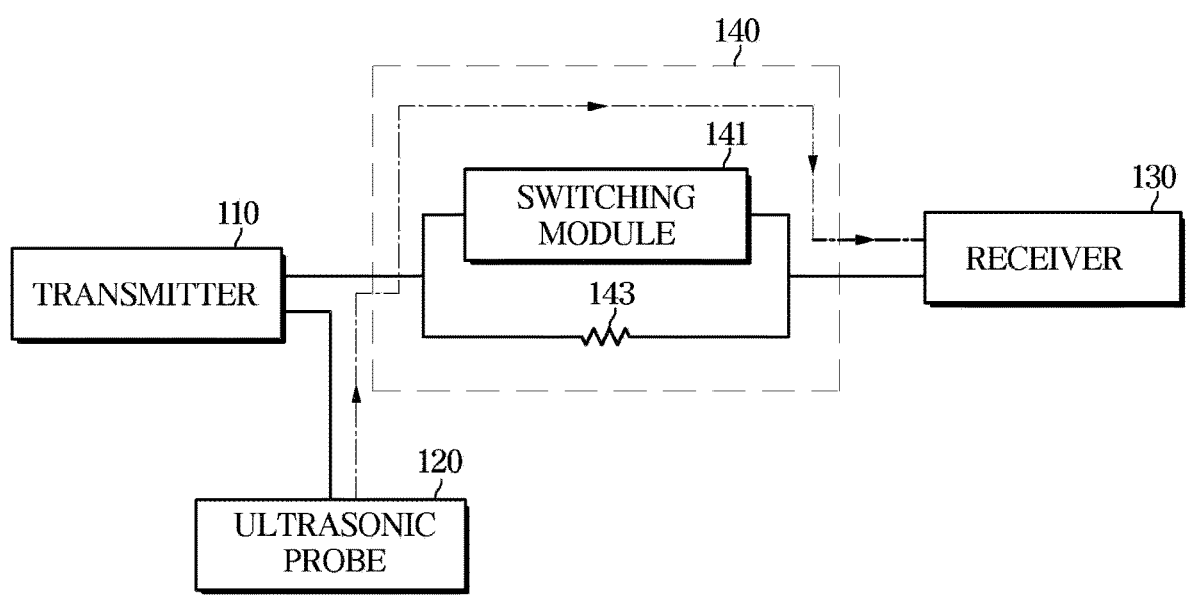
FIG. 7 is a view for describing a flow of a reception signal in a reception section according to exemplary embodiments of the disclosure.

FIG. 5 is a block diagram of an ultrasonic apparatus according to exemplary embodiments of the disclosure, FIG. 6 is a view for describing a flow of a transmission signal in a transmission section according to exemplary embodiments of the disclosure, and FIG. 7 is a view for describing a flow of a reception signal in a reception section according to exemplary embodiments of the disclosure.

Referring to FIGS. 5 to 7, the transceiver switching circuit 140 may be connected to the transmitter 110, the ultrasonic probe 120, and the receiver 130. Particularly, one end of the transceiver switching circuit 140 may be connected to the transmitter 110 and the ultrasonic probe 120, and the other end of the transceiver switching circuit 140 may be connected to the receiver 130.

The transceiver switching circuit 140 may include a switching module 141 and a resistor 143. The switching module 141 and the resistor 143 may be disposed in parallel and connected to the transmitter 110, the ultrasonic probe 120, and the receiver 130.

The transceiver switching circuit 140 may further include the resistor 143 as compared to the transceiver switching circuit 40 of the conventional ultrasonic apparatus, and the switching module 141 of the transceiver switching circuit 140 may perform the same operation as the transceiver switching circuit 40 of the conventional ultrasonic apparatus.

In detail, the switching module 141 may perform an operation of blocking the transmission signal output from the transmitter 110 and transmitting the reception signal output from the ultrasonic probe 120 to the receiver 130. The resistor 143 of the transceiver switching circuit 140 may be disposed between the transmitter 110 and receiver 130 to attenuate a voltage level of the transmission signal to match the input range of the receiver 130.

In the transmission section in which the transmitter 110 outputs the transmission signal, the transceiver switching circuit 140 may operate to deactivate the switching module 141 so that the transmission signal is attenuated through the resistor 143 and transmitted to the receiver 130. In the reception section in which the ultrasonic probe 120 outputs the reception signal, the transceiver switching circuit 140 may operate to activate the switching module 141 so that the reception signal is transmitted to the receiver 130 without attenuation through the switching module 141.

Referring to FIG. 6, in the transmission section in which the transmitter 110 transmits the transmission signal, the transmission signal may be transmitted to the ultrasonic probe 120 and transmitted to the receiver 130 in attenuated state through the resistor 143 of the transceiver switching circuit 140.

In detail, in the transmission section in which the transmitter 110 transmits the transmission signal, the transmission signal may be transmitted to the ultrasonic probe 120. Since a resistance value of the resistor 143 is larger than an impedance of a transmission circuit including the ultrasonic probe 120 and the cable 180, the resistance value of the resistor 143 does not affect the transmission performance of the ultrasonic apparatus 100.

The transmission signal transmitted to the ultrasonic probe 120 may be converted into the ultrasonic signal by the transducer of the ultrasonic probe 120. The converted ultrasonic signal may be transmitted from the ultrasonic probe 120 to the object and reflected from the object to form the ultrasonic echo signal.

In addition, in the transmission section in which the transmitter 110 transmits the transmission signal, the transmission signal may be transmitted to the receiver 130 through the resistor 143. The transmission signal transmitted to the receiver 130 may pass through the resistor 143 and may be attenuated according to a ratio of input impedances of the resistor 143 and the receiver 130. Particularly, the voltage level of the transmission signal transmitted to the receiver 130 may be attenuated according to the ratio of the input impedance of the resistor 143 and the receiver 130 as illustrated in [Equation 1] below.

$$V_s' = V_s \times \frac{R_{in}}{R_s + R_{in}} \quad \text{[Equation 1]}$$

In [Equation 1], $V_s'$ may denote the voltage of the attenuated transmission signal, $V_s$ may denote the voltage of the transmission signal, $R_{in}$ may denote the input impedance of the receiver 130, and $R_s$ may denote the resistance value of the resistor 143. The resistance value of resistor 143 may be determined such that the voltage level of the transmission signal does not exceed the input range of receiver 130.

The transmission signal output from the transmitter 110 may be transmitted to the transceiver switching circuit 140. The transceiver switching circuit 140 may deactivate the switching module 141 to allow the transmission signal to pass through the resistor 143 connected in parallel with the switching module 141. The deactivation of the switching module 141 may refer to an open state in which the transmitter 110 and the receiver 130 are not connected through the switching module 141 to block both the transmission signal and the reception signal.

Through this, the transmission signal may be transmitted to the receiver 130 in the attenuated state only through the resistor 143 and not through the switching module 141. In addition, transmission of the non-attenuated transmission signal to the receiver 130 may be completely blocked through deactivation of the switching module 141.

The receiver 130 may receive the attenuated transmission signal through resistor 143 of transceiver switching circuit 140. The receiver 130 may process the attenuated transmission signal through the existing amplifier and ADC without the separate additional amplifier and ADC.

The attenuated transmission signal may be amplified in the amplifier of the receiver 130, converted into the digital signal in the ADC of the receiver 130, and analyzed in the digital signal processor of the receiver 130. Through this, the receiver 130 may obtain the transmission waveform information based on the attenuated transmission signal. This uses an existing reception signal path of the receiver 130 as it is and does not require an additional reception channel.

Referring to FIG. 7, in the reception section in which the ultrasonic probe 120 outputs the reception signal, the reception signal may be transmitted to the receiver 130 through the switching module 141 of the transceiver switching circuit 140.

In detail, in the reception section in which the ultrasonic probe 120 outputs the reception signal, the reception signal may be transmitted from the ultrasonic probe 120 to the transceiver switching circuit 140. The reception signal transmitted to the transceiver switching circuit 140 may be transmitted to the receiver 130 without attenuation through the switching module 141 of the transceiver switching circuit 140.

The transceiver switching circuit 140 may operate to activate the switching module 141 so that the reception signal is transmitted to the receiver 130 without attenuation through the switching module 141. The activation of the switching module 141 may refer to a state in which the transmission signal is blocked and the reception signal is passed.

Since the resistance value of the resistor 143 is larger than the impedance in the activated state of the switching module 141, the resistance value of the resistor 143 does not affect the reception performance of the ultrasonic apparatus 100. Through this, the reception signal may be transmitted to the receiver 130 without attenuation through the switching module 141 without passing through the resistor 143.

The receiver 130 may receive the reception signal without attenuation through the switching module 141 of the transceiver switching circuit 140. The receiver 130 may process the reception signal through the amplifier and the ADC. The reception signal may be amplified by the amplifier of the receiver 130, converted the signal into the digital signal by the ADC of the receiver 130, and analyzed by the digital signal processor of the receiver 130. In this way, the receiver 130 may obtain the ultrasonic image through the reception signal.

Figure 8:
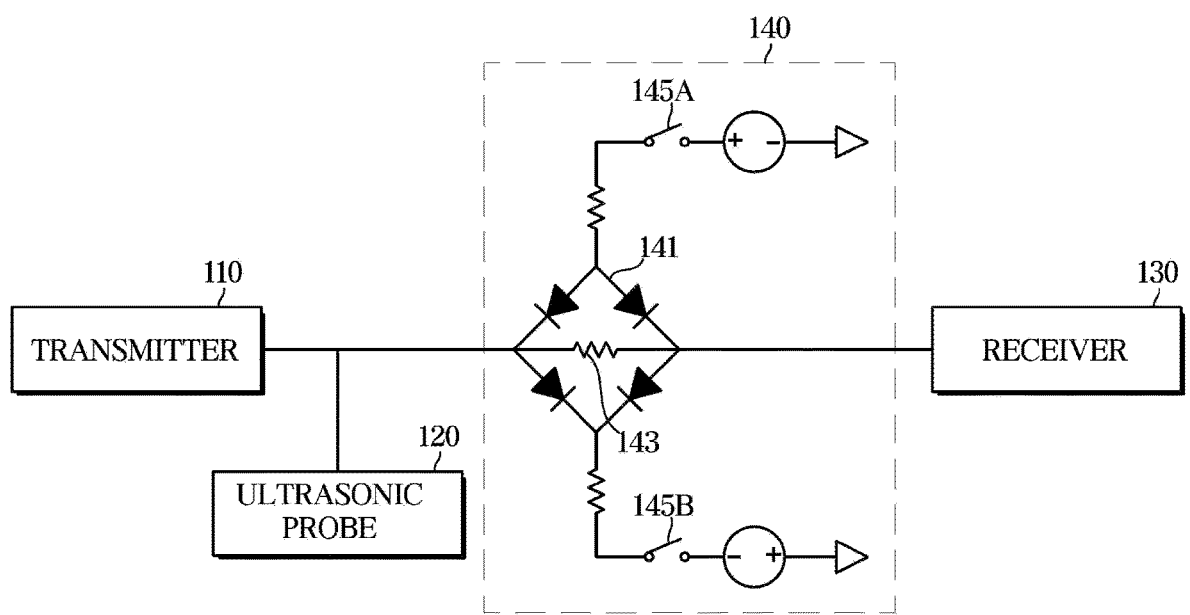
FIG. 8 is a circuit diagram of an ultrasonic apparatus according to exemplary embodiments of the disclosure.
Figure 9:
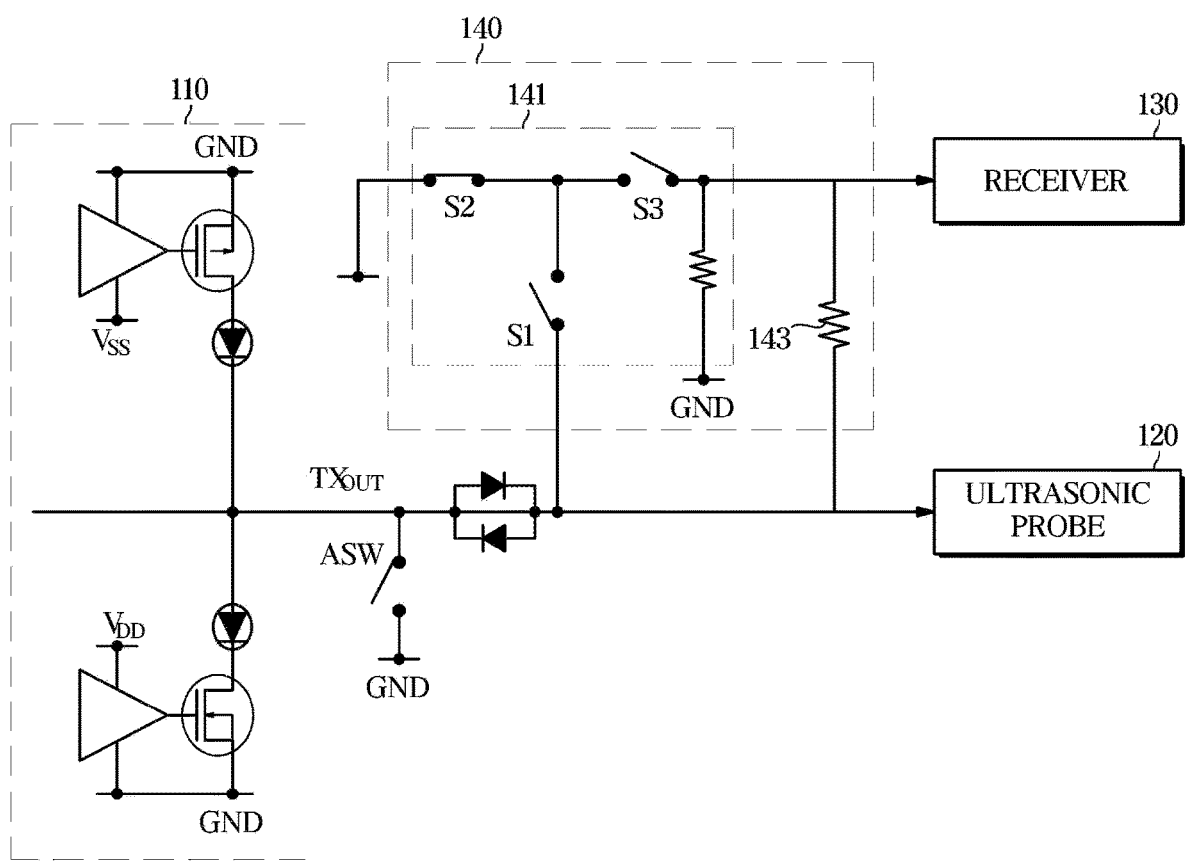
FIG. 9 is another circuit diagram of an ultrasonic apparatus according to exemplary embodiments of the disclosure.

FIG. 8 is a circuit diagram of an ultrasonic apparatus according to exemplary embodiments of the disclosure, and FIG. 9 is another circuit diagram of an ultrasonic apparatus according to exemplary embodiments of the disclosure.

Referring to FIG. 8, the ultrasonic apparatus 100 may include the transmitter 110, the ultrasonic probe 120, the receiver 130, and the transceiver switching circuit 140. The transceiver switching circuit 140 may include the switching module 141, the resistor 143, a first switch 145A, and a second switch 145B.

The switching module 141 may include a diode bridge that is switchable between a first state and a second state. The switching module 141 may apply a reverse bias current to the diode bridge in the first state to block transmission of the transmission signal to the receiver 30, and may operate a forward bias current to the diode bridge in the second state so that the reception is transmitted to the receiver 30.

To this end, the controller 150 may control a voltage source of the switching module 141 to apply the reverse bias current or the forward bias current to the diode bridge.

The resistor 143 may be disposed in parallel with the switching module 141 and connected to the transmitter 110, the ultrasonic probe 120, and the receiver 130. Particularly, one end of the resistor 143 may be connected to the diode bridge, the transmitter 110, and the ultrasonic probe 120 and the other end of the resistor 143 may be connected to the diode bridge and the receiver 130. The resistor 143 may be disposed between the transmitter 110 and the receiver 130 to attenuate the voltage level of the transmission signal to match the input range of the receiver 130.

In the transmission section in which the transmitter 110 outputs the transmission signal, the transceiver switching circuit 140 may operate to deactivate the switching module 141 so that the transmission signal is attenuated through the resistor 143 and transmitted to the receiver 130. In the reception section in which the ultrasonic probe 120 outputs the reception signal, the transceiver switching circuit 140 may operate to activate the switching module 141 so that the reception signal is transmitted to the receiver 130 without attenuation through the switching module 141.

The first switch 145A and the second switch 145B of the transceiver switching circuit 140 may operate for switching between deactivation and activation of the switching module 141.

Particularly, the first switch 145A and the second switch 145B may be opened in the transmission section in which the transmitter 110 outputs the transmission signal to deactivate the switching module 141. Through this, the transmission signal and the reception signal may not be transmitted to the receiver 130 through the switching module 141.

In addition, the first switch 145A and the second switch 145B may be shorted in the reception section in which the ultrasonic probe 120 outputs the reception signal to activate the switching module 141. Through this, the transmission signal may be blocked from being transmitted to the receiver 130 and the reception signal may be operated to be transmitted to the receiver 130.

Referring to FIG. 9, the ultrasonic apparatus 100 may include the transmitter 110, the ultrasonic probe 120, the receiver 130, and the transceiver switching circuit 140. The transceiver switching circuit 140 may include the switching module 141 and the resistor 143.

The switching module 141 may include switches S1, S2, and S3 that are switchable between the first state and the second state. The switching module 141 may control each of the switches S1, S2, and S3 to operate in one of an open state and a short state. In addition, the switches S1, S2, and S3 of the switching module 141 may be controlled by the controller 150.

The switching module 141 may operate to block the transmission of the transmission signal to the receiver 130 by adjusting at least one of the switches S1 and S3 to the open state so that the transmitter 110 and the receiver 130 are not connected through the switching module 141 in the first state. The switching module 141 may operate to transmit the reception signal to the receiver 130 by adjusting the switches S1 and S3 to the short state and adjusting the switch S2 to the open state so that the transmitter 110 and the receiver 130 are connected through the switching module 141 in the second state.

FIG. 9 illustrates an embodiment of the switching module 141 that includes three switches S1, S2, and S3, the disclosed embodiment is exemplary and should not be construed as limiting.

The transceiver switching circuit 140 may operate to deactivate the switching module 141 in the transmission section in which the transmitter 110 outputs the transmission signal so that the transmission signal is attenuated through the resistor 143 and transmitted to the receiver 130.

The transceiver switching circuit 140 may operate to activate the switching module 141 in the reception section in which the ultrasonic probe 120 outputs the reception signal so that the reception signal is transmitted to the receiver 130 without attenuation through the switching module 141.

The switching module 141 may operate to block the transmission signal from being transmitted to the receiver 130 and transmit the reception signal to the receiver 130 by adjusting at least one switch so that the transmitter 110 and the receiver 130 are not connected through the switching module 141 in a deactivation state and adjusting at least one switch in an activation state.

Figure 10:
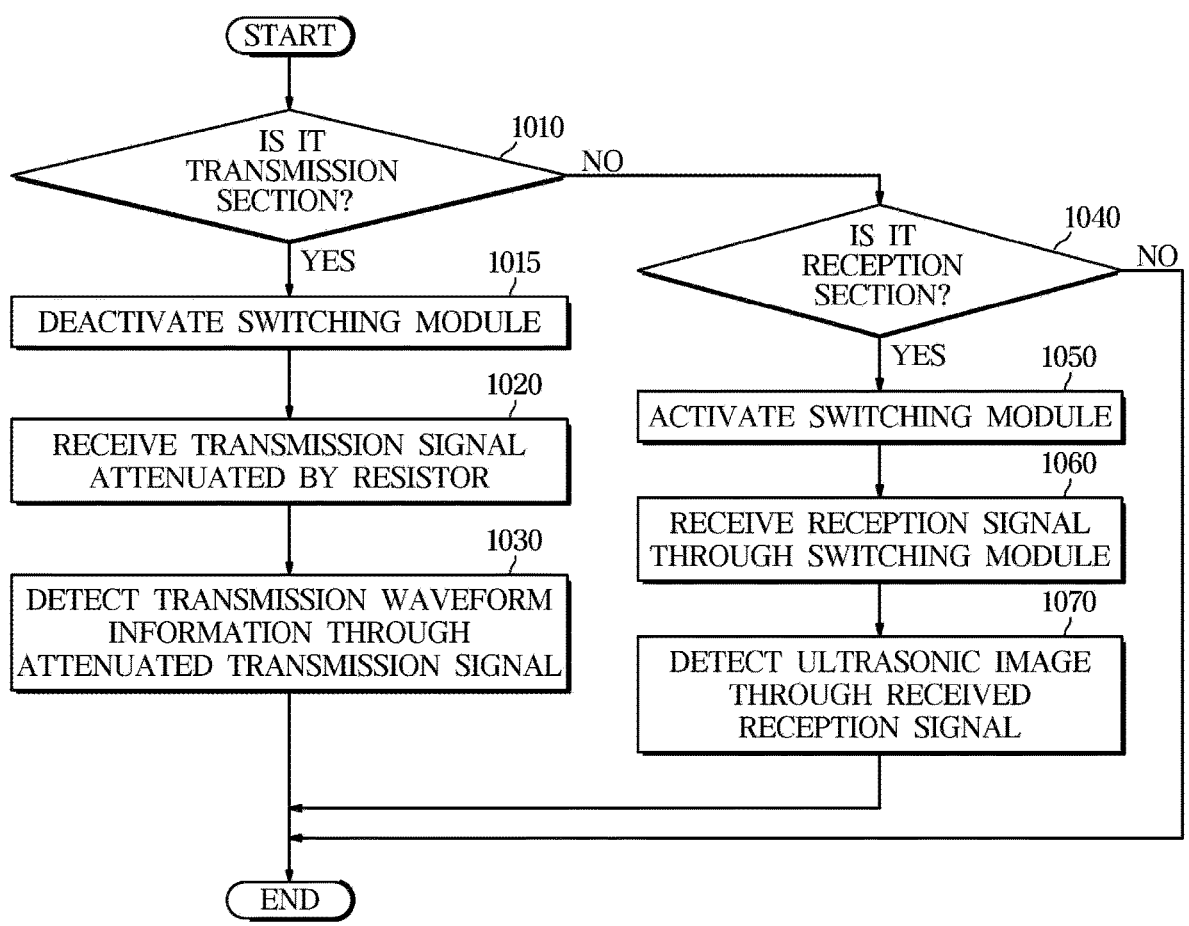
FIG. 10 is a flowchart illustrating a method of controlling an ultrasonic apparatus according to exemplary embodiments of the disclosure.
Figure 11:
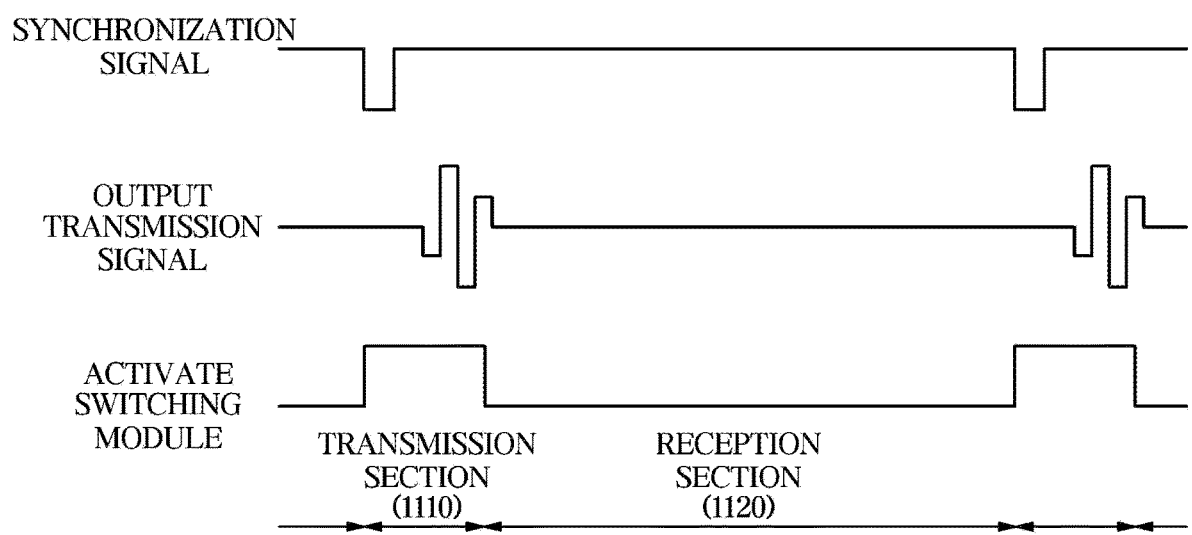
FIG. 11 is a view for describing a transmission section and a reception section according to exemplary embodiments of the disclosure.

FIG. 10 is a flowchart illustrating a method of controlling an ultrasonic apparatus according to exemplary embodiments of the disclosure, FIG. 11 is a view for describing a transmission section and a reception section according to exemplary embodiments of the disclosure, and FIG. 12 is a graph illustrating a transmission waveform according to exemplary embodiments of the disclosure.

Referring to FIG. 10, the ultrasonic apparatus 100 may determine whether it corresponds to the transmission section (1010). In the transmission section, the transmitter 110 of the ultrasonic apparatus 100 may output the transmission signal. In addition, according to an embodiment, the transmission section may include a section in which the synchronization signal which is a reference for output of the transmission signal is output.

In the case of the transmission section in which the transmitter 110 outputs the transmission signal (YES in 1010), the ultrasonic apparatus 100 may deactivate the switching module 141 of the transceiver switching circuit 140 (1015).

Particularly, when it is identified that the ultrasonic apparatus 100 corresponds to the transmission section, the controller 150 of the ultrasonic apparatus 100 may control the switching module 141 to be deactivated. The deactivation of the switching module 141 may refer to a state in which the transmitter 110 is not connected to the receiver 130 through the switching module 141.

Referring to FIG. 11, the transmitter 110 may output the transmission signal by delaying a time set based on a synchronization signal having a pulse repetition frequency (PRF). In the transmission section 1110 including a section in which the synchronization signal is output and a section in which the transmission signal is output, the switching module 141 of the transceiver switching circuit 140 may be deactivated.

When the switching module 141 is deactivated, the ultrasonic apparatus 100 may receive the transmission signal attenuated by the resistor 143 (1015). In detail, the transmission signal output from the transmitter 110 may be received to the receiver 130 in the attenuated state made by the resistor 143 of the transceiver switching circuit 140. The voltage level of the attenuated transmission signal may be attenuated so as not to exceed the input range of the receiver 130.

The ultrasonic apparatus 100 may detect the transmission waveform information through the attenuated transmission signal (1030). In detail, the receiver 130 of the ultrasonic apparatus 100 may receive the attenuated transmission signal and analyze the attenuated transmission signal to detect the transmission waveform information. The receiver 130 may amplify the attenuated transmission signal by the amplifier, convert the signal into the digital signal by the ADC, and analyze the digital signal by the digital signal processor.

The transmission waveform information may include at least one of information about the waveform of the transmission signal, the amplitude of the transmission signal, a frequency of the transmission signal, and a generation time of the transmission signal based on the synchronization signal. The controller 150 of the ultrasonic apparatus 100 may control the display 170 to display the detected transmission waveform information.

Referring to FIG. 12, the display 170 may display the detected transmission waveform information according to an embodiment. FIG. 12A illustrates the waveform of the transmission signal obtained using the conventional transceiver switching circuit 40. Since the conventional transceiver switching circuit 40 is intended to block the transmission signal, it is difficult to receive the transmission signal without distortion. Since the waveform of the transmission signal obtained using the conventional transceiver switching circuit 40 is distorted by a blocking operation of the transceiver switching circuit 40, it is not possible to identify the information about the waveform of the transmission signal, the amplitude of the transmission signal, and the generation time of the transmission signal based on the synchronization signal.

FIG. 12B illustrates waveforms of the transmission signal obtained using the transceiver switching circuit 140 according to an embodiment. Since the receiver 130 receives the transmission signal attenuated by the resistor 143 of the transceiver switching circuit 140, the receiver 130 may detect the waveform of the transmission signal in which the amplitude and frequency are not damaged.

Particularly, through the waveform of the transmission signal obtained using the transceiver switching circuit 140 according to an embodiment, the user may identify the amplitude of the transmission signal including a peak value of the voltage, and may identify the information about the generation time of the transmission time based on the synchronization signal.

In addition, the user may identify the frequency of the transmission signal by changing the waveform over time. The user may identify that the voltage of the transmission signal is in an intended range through the waveform and amplitude of the transmission signal.

In addition, the user may obtain not only the waveform of the transmission signal but also transmission signal generation time information based on a transmission synchronization signal, so that the user may identify a transmission focus state.

As such, the ultrasonic apparatus 100 may analyze the transmission signal in real time and measure the amplitude and a transmission timing of the transmission signal for each transmission channel. Through this, the user of the ultrasonic apparatus 100 may be protected from heat generation of a surface temperature of the ultrasonic probe 120 due to abnormal output of the transmission signal and excessive energy of the ultrasonic signal irradiated to the human body.

In addition, it is possible to prevent the performance error of the ultrasonic apparatus 100 generated by the transmission signal is transmitted differently than intended to prevent diagnostic errors.

Referring back to FIG. 10, when it is not the transmission section in which the transmitter 110 outputs the transmission signal (NO in 1010), the ultrasonic apparatus 100 may identify whether it corresponds to the reception section (1040). In the reception section, the ultrasonic probe 120 may output the reception signal based on the ultrasonic echo signal reflected from the object.

In the case of the reception section in which the ultrasonic probe 120 outputs the reception signal (YES in 1040), the ultrasonic apparatus 100 may activate the switching module 141 of the transceiver switching circuit 140 (1050).

Particularly, when it is identified that the ultrasonic apparatus 100 corresponds to the reception section, the controller 150 of the ultrasonic apparatus 100 may control the switching module 141 to be activated. The activation of the switching module 141 may refer to the state in which the transmitter 110 is connected to the receiver 130 through the switching module 141. In detail, the switching module 141 may be activated to block the transmission of the transmission signal to the receiver 130 and to transmit the reception signal to the receiver 130.

Referring to FIG. 11, the switching module 141 may be activated in the reception section 1120 in which the ultrasonic probe 120 outputs the reception signal. Particularly, in the case of the reception section 1120 rather than the transmission section 1110, the switching module 141 of the transceiver switching circuit 140 may be activated.

When the switching module 141 is activated, the ultrasonic apparatus 100 may receive the reception signal through the switching module 141 (1060). In detail, the reception signal output from the ultrasonic probe 120 may be received by the receiver 130 without being attenuated through the switching module 141 of the transceiver switching circuit 140.

The ultrasonic apparatus 100 may detect the ultrasonic image through the received reception signal (1070). In detail, the receiver 130 of the ultrasonic apparatus 100 may receive the attenuated transmission signal and analyze the attenuated transmission signal to detect the transmission waveform information.

The receiver 130 may amplify the reception signal by the amplifier, convert the signal into the digital signal by the ADC, and analyze the digital signal by the digital signal processor. In this way, the receiver 130 may detect the ultrasonic image based on the reception signal. The controller 150 of the ultrasonic apparatus 100 may control the display 170 to display the detected ultrasonic image.

As described above, since the ultrasonic apparatus 100 may deactivate the switching module 141 in the transmission section and activate the switching module 141 in the reception section, a transmission operation error detection in the operation of the ultrasonic apparatus 100 may be possible in real time.

Figure 13:
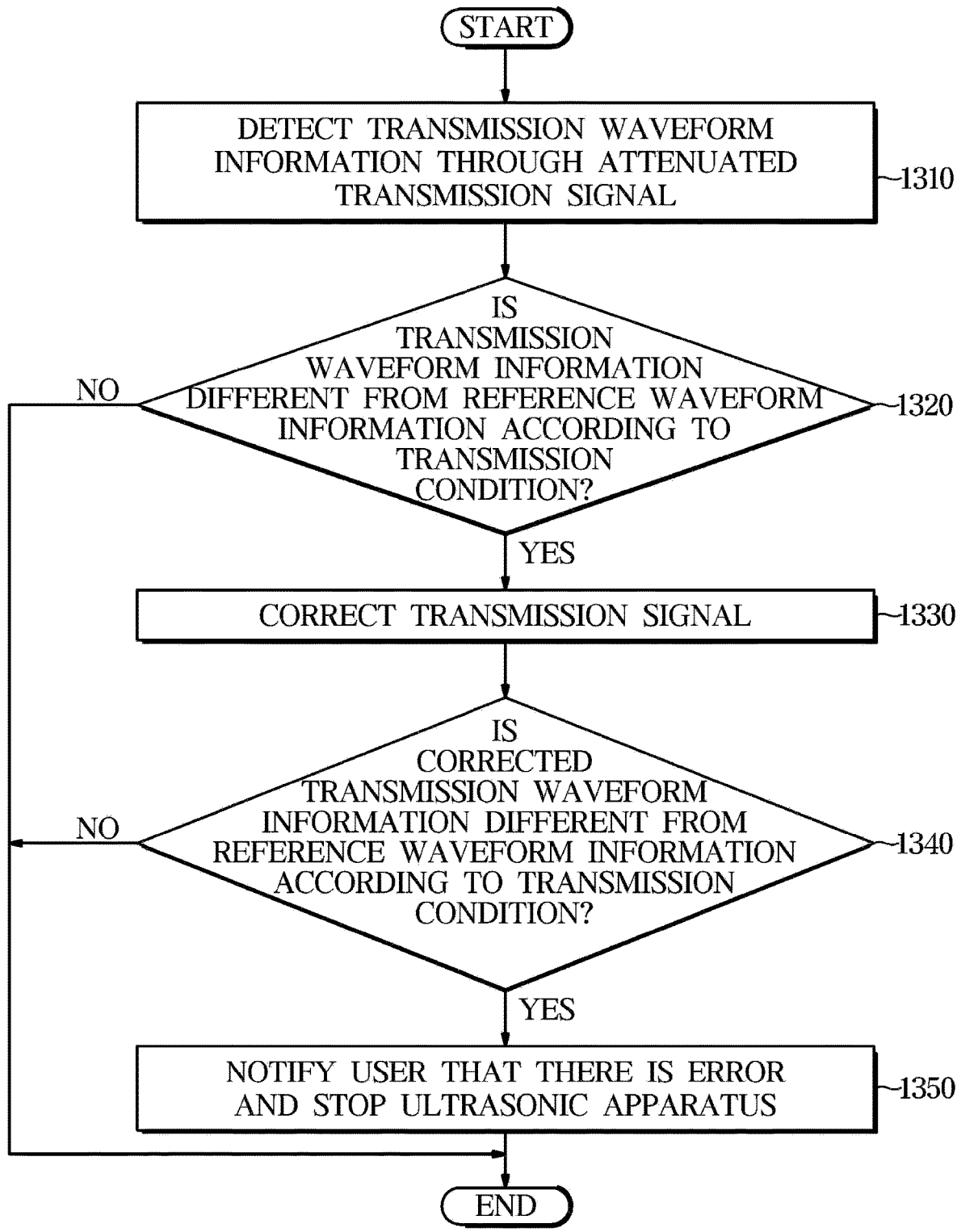
FIG. 13 is a flowchart illustrating a method of controlling an ultrasonic apparatus according to exemplary embodiments of the disclosure.

FIG. 13 is a flowchart illustrating a method of controlling an ultrasonic apparatus according to exemplary embodiments of the disclosure.

Referring to FIG. 13, the ultrasonic apparatus 100 may detect the transmission waveform information through the attenuated transmission signal (1310). In detail, the receiver 130 of the ultrasonic apparatus 100 may receive the transmission signal output from the transmitter 110 in the attenuated state through the resistor 143 of the transceiver switching circuit 140.

The receiver 130 may detect the transmission waveform information by amplifying the attenuated transmission signal by the amplifier, converting the signal into the digital signal by the ADC, and analyzing the digital signal by the digital signal processor.

The ultrasonic apparatus 100 may determine whether the transmission waveform information is different from the reference waveform information according to the transmission condition (1320). In detail, the controller 150 of the ultrasonic apparatus 100 may receive the transmission waveform information obtained from the receiver 130 and determine whether the transmission waveform information is different from the reference waveform information according to the transmission condition. The controller 150 may compare the information on the generation time of the transmission signal based on the waveform of the transmission signal, the amplitude of the transmission signal, and the synchronization time with the reference waveform information.

Through this, the controller 150 of the ultrasonic apparatus 100 may continuously identify whether the ultrasonic apparatus 100 is normally operated based on the comparison result, and may identify the normal operation of the ultrasonic apparatus 100 whenever the transmission condition is changed, thereby correcting the stability.

To this end, the controller 150 may store the plurality of reference waveform information corresponding to each of the plurality of transmission conditions. The reference waveform information may refer to information of the transmission waveform intended by the user in a corresponding transmission condition.

The transmission condition may be input through the inputter 160 as a condition of the transmission signal intended by the user. The transmission condition may vary according to the diagnosis portion, the diagnosis type, the mode for the ultrasonic image, and the like, and generally include the amplitude magnitude of the transmission signal, the frequency, and the generation time of the transmission signal based on the synchronization signal.

When the transmission waveform information is different from the reference waveform information (YES in 1320), the ultrasonic apparatus 100 may correct the transmission signal corresponding to the detected transmission waveform information (1330). Particularly, when the detected transmission waveform information and the reference waveform information according to the transmission conditions are different, the controller 150 of the ultrasonic apparatus 100 may control the transmitter 110 to output the transmission signal having the same waveform information as the reference waveform information corresponding to the transmission condition.

The transmitter 110 may adjust the voltage gain of the transmission signal or the output delay time based on the control of the controller 150 to correct the transmission signal so that the transmission signal has the same waveform information as the reference waveform information corresponding to the transmission condition. Through this, the plurality of transmission channels of the ultrasonic apparatus 100 may output the transmission signal having a uniform waveform size of the transmission signal between the channels.

According to another embodiment, when the transmission waveform information is different from the reference waveform information (YES in 1320), the controller 150 of the ultrasonic apparatus 100 may control the display 170 to notify the user that there is the error, and may stop the ultrasonic apparatus 100.

The ultrasonic apparatus 100 may determine whether the corrected transmission waveform information is different from the reference waveform information according to the transmission condition (1340). In detail, the controller 150 of the ultrasonic apparatus 100 may receive the corrected transmission waveform information from the receiver 130 and determine whether the corrected transmission waveform information is different from the reference waveform information according to the transmission condition. Through this, the ultrasonic apparatus 100 may identify whether the transmission signal output from the transmitter 110 is output according to the intended transmission condition.

When the corrected transmission waveform information is different from the reference waveform information according to the transmission condition (YES in 1340), the ultrasonic apparatus 100 may control the display 170 to notify the user that there is the error, and may stop the ultrasonic apparatus 100.

Particularly, the controller 150 of the ultrasonic apparatus 100 may identify that the ultrasonic apparatus 100 is abnormally operated when the waveform of the corrected transmission signal output from the transmitter 110 is different from the reference waveform according to the transmission condition. The controller 150 of the ultrasonic apparatus 100 may control the display 170 to notify the user that the ultrasonic apparatus 100 is the error, and may stop the operation of the ultrasonic apparatus 100.

According to another embodiment, when the corrected transmission waveform information is different from the reference waveform information according to the transmission condition, the ultrasonic apparatus 100 may again correct the transmission signal corresponding to the corrected transmission waveform information. FIG. 13 illustrates an embodiment in which a process of correcting the transmission signal is performed once, the disclosed embodiment is exemplary, and the process of correcting the transmission signal may be performed one or more times according to the user's setting.

Hereinafter, in the ultrasonic apparatus 100 including the plurality of channels 101-1, 101-2, ..., and 101-N, referring to FIGS. 14 to 17, when the transmission waveform information detected in the specific channels 101-1, 101-2, ..., and 101-N is different from the reference waveform information, the ultrasonic image correction process for stopping only the specific channel (e.g., one of 101-1, 101-2, ..., 101-N) having the error and solving the error of the ultrasonic image due to the stop of the channel will be described.

Figure 14:
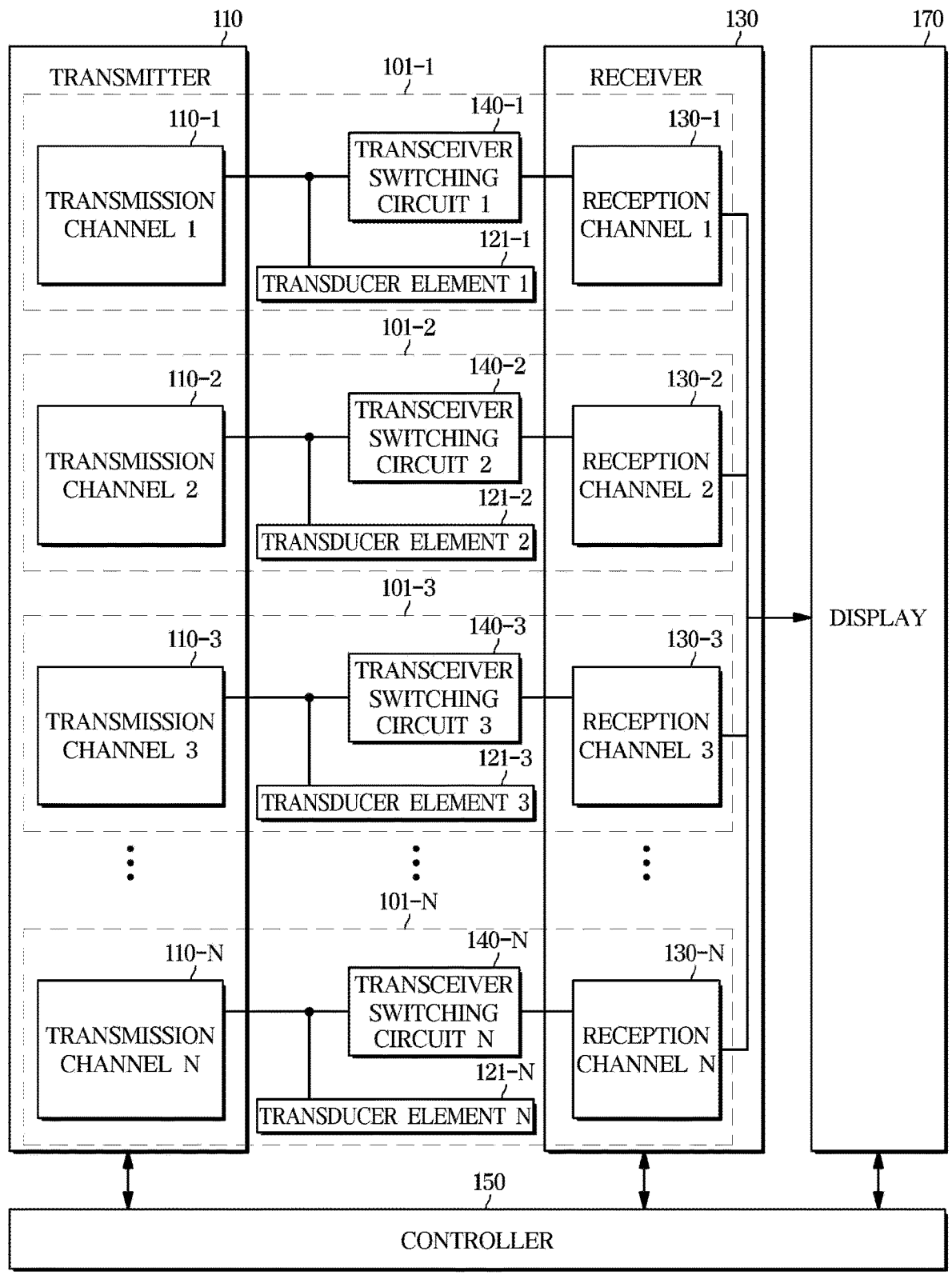
FIG. 14 is a block diagram of an ultrasonic apparatus including a plurality of channels according to exemplary embodiments of the disclosure.

FIG. 14 is a block diagram of an ultrasonic apparatus including a plurality of channels according to exemplary embodiments of the disclosure.

Referring to FIG. 14, the plurality of channels 101-1, 101-2, ..., and 101-N may include the transmission channel 110-1, 110-2, ..., and 110-N for generating and outputting the transmission signal based on the synchronization signal, the transducer elements 121-1, 121-2, ..., and 121-N for converting the transmission signal output from the transmission channels 110-1, 110-2, ..., and 110-N into the ultrasonic signal and outputting the ultrasonic signal, the transceiver switching circuits 140-1, 140-2, ..., and 140-N for attenuating and outputting the transmission signal from the transmission channels 110-1, 110-2, ..., and 110-N and transmitting the ultrasonic signal to the object and outputting the reception signal reflected from the object, the reception channels 130-1, 130-2, ..., and 130-N for receiving the attenuated output transmission signal and the output reception signal and detecting the transmission waveform information based on the attenuated transmission signal.

In other words, the transceiver switching circuits 140-1, 140-2, ..., and 140-N may be included in each of the plurality of channels 101-1, 101-2, ..., and 101-N, and thus the reception channels 130-1, 130-2, ..., and 130-N included in each of the plurality of channels 101-1, 101-2, ..., and 101-N may detect the transmission waveform information of each of the transmission channels 110-1, 110-2, ..., 110-N.

For convenience of explanation, it is assumed that the transmission waveform information of transmission channel 2 110-2 is different from the reference waveform information.

The transmission signal output from the transmission channel 2 110-2 may be converted into the ultrasonic signal by the transducer element 2 121-2 and output the ultrasonic signal. The transmission signal output from the transmission channel 2 110-2 may be attenuated and output, and the reception channel 2 130-2 may detect the transmission waveform information through the transceiver switching circuit 2 140-2 that transmits the ultrasonic signal to the object and outputs the reception signal reflected from the object.

The controller 150 may store the reference waveform information according to the transmission condition, and compare the transmission waveform information detected in the reception channel 2 130-2 with the reference waveform information. When the detected transmission waveform information is different from the reference waveform information, the controller 150 may stop the operation of the transmission channel 2 110-2.

When the operation of the transmission channel 2 110-2 is stopped, the transmission channel 2 110-2 may not generate and output the transmission signal, and thus the reception channel 2 130-2 may not receive any reception signal. Therefore, the reception channel 2 130-2 may not obtain ultrasonic image data based on the reception signal.

At this time, the reception channel 2 130-2 may obtain the ultrasonic image data based on the reception signal received by at least one of reception channel 1 130-1 or reception channel 3 130-3, which correspond to channels adjacent to the reception channel 2 130-2, according to the control of the controller 150. For the sake of convenience in description, the channels adjacent to channel 2 101-2 are assumed to be channel 1 101-1 and channel 3 101-3, but the channels adjacent to channel 2 101-2 may be more than or less than two channels. The number of the adjacent channels may vary depending on whether the plurality of transducer elements 121 of the ultrasonic probe 120 form a two-dimensional (2D) transducer array or a one-dimensional (1D) transducer array and may vary depending on the position of the transducer element 121-2 of the channel 2 101-2 as will be described below with reference to FIG. 15.

In addition, when the transmission waveform information of the transmission channel 2 110-2 is different from the reference waveform information, the controller 150 may control the display 170 to display that the channel including the transmission channel 2 110-2 has the error.

As such, according to the embodiment of the disclosure, when the error occurs in the transmission channel 2 110-2, the reception channel 2 130-2 may obtain the ultrasonic image data based on at least one of the reception signal of the reception channel 1 130-1 and the reception signal of the reception channel 3 130-3 to prevent a dark line defect of the ultrasonic image, and the display 170 may display that the error has occurred in the transmission channel 2 110-2, thereby allowing the user to repair the transmission channel 2 110-2.

Hereinafter, a channel adjacent to the channel 2 101-2 among the plurality of channels 101-1, 101-2, . . . , 101-N will be described with reference to FIG. 15.

Figure 15:
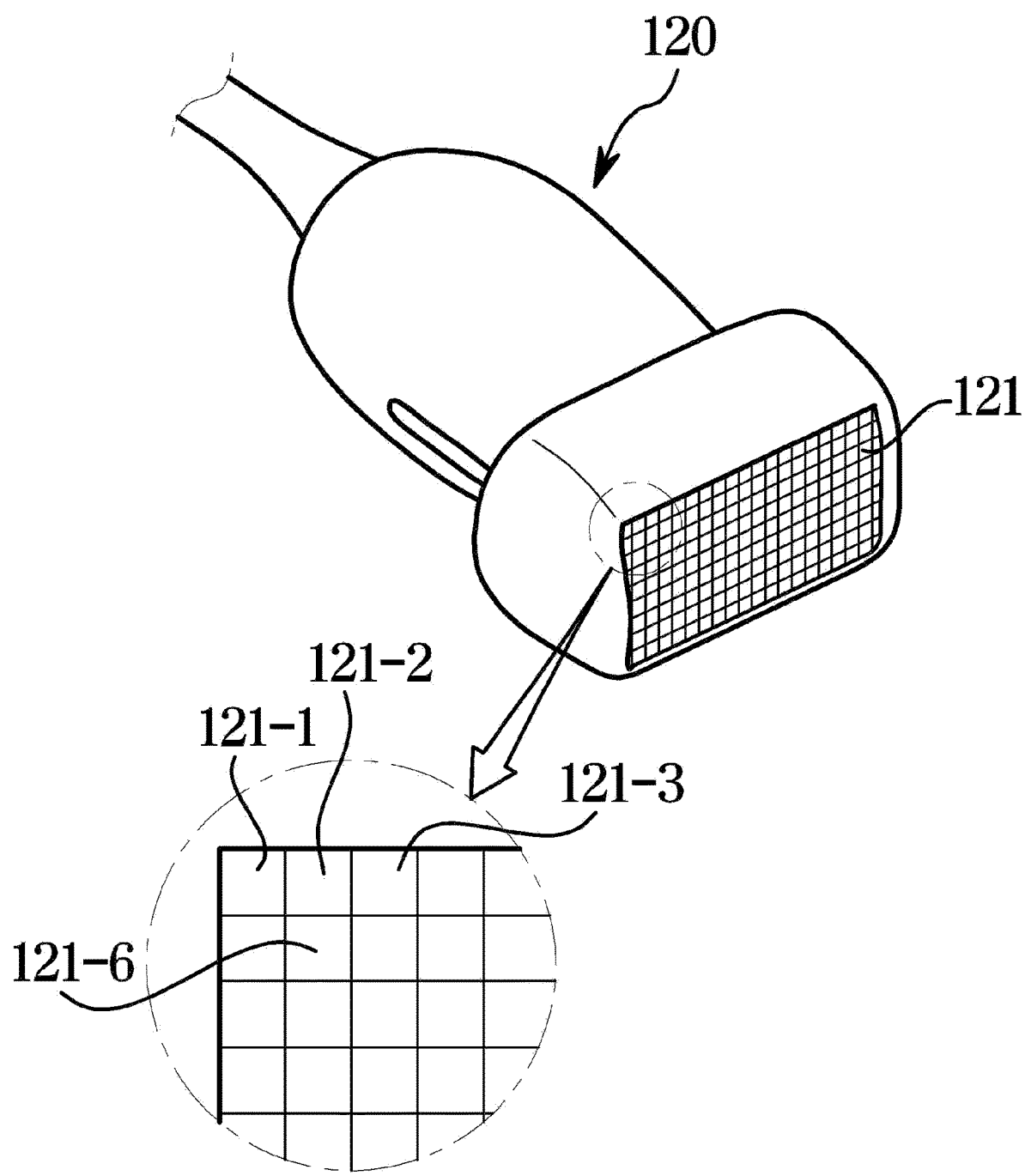
FIG. 15 is a view illustrating an exterior of an ultrasonic probe including a two-dimensional (2D) array transducer according to exemplary embodiments of the disclosure.

FIG. 15 is a view illustrating an exterior of an ultrasonic probe including a two-dimensional (2D) array transducer according to exemplary embodiments of the disclosure.

Referring to FIG. 15, the ultrasonic probe 120 may include the plurality of transducer elements 121. The plurality of transducer elements 121 may be connected to the plurality of transmission channels 110-1, 110-2, . . . , and 110-N and the plurality of reception channels 130-1, 130-2, . . . , and 130-N, as described above. The plurality of transducer elements 121 may be implemented in a one-dimensional (1D) array, and arranged in a linear form or in a convex form. In both cases, the basic operation principle of the ultrasonic probe is the same, but in the case of the convex type probe, since the ultrasonic signals are radiated from the plurality of transducer elements 121 in a fan-shape, the generated ultrasonic image may also have a fan-shape.

The plurality of transducer elements 121 may be implemented in a two-dimensional (2D) array, as illustrated in FIG. 15. In this case, the transducer element 1 121-2 connected to the transmission channel 2 110-2 may be arranged as illustrated in FIG. 15, and transducer elements adjacent to the transducer element 2 121-2 may include the transducer element 1 121-1, the transducer element 3 121-3, and the transducer element 6 121-6.

In other words, in the plurality of channels 101-1, 101-2, . . . , and 101-N, channels adjacent to a specific channel 101-2 may be one or more channels 101-1, 101-3, and 101-6 including the transducer elements 121-1, 121-3, and 121-6 adjacent to the transducer element 121-2 of the specific channel 101-2. That is, when the transducer elements 121 are adjacent to each other, the positional difference of ultrasonic signals transmitted from the transducer elements 121 to an object is small, and thus reception signals received by the reception channels 130-1, 130-2, 130-3, and 130-6 merely have a small difference from each other. Accordingly, when an error occurs in a specific transmission channel 110-2, in order to correct the dark line defect in the ultrasonic image caused by the stopped operation of the transmission channel 110-2, ultrasonic image data is obtained based on the reception signals of the adjacent channels 101-1, 101-3, and 101-6.

Hereinafter, referring to FIGS. 16A to 16B, an ultrasonic image corrected with regard to the dark line defect according to the embodiment of the disclosure is described.

Figure 16A:
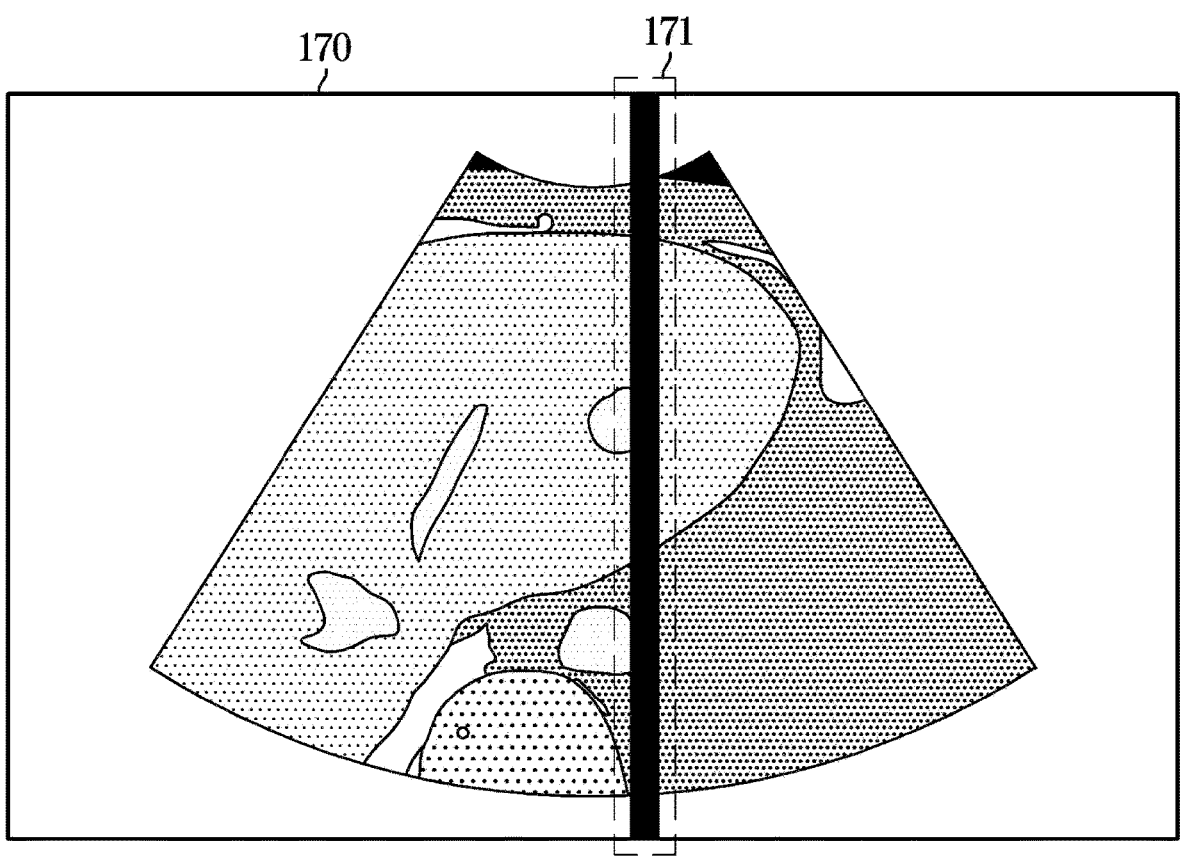
FIGS. 16A and 16B are views for describing an image correction process of an ultrasonic apparatus according to exemplary embodiments of the disclosure.
Figure 16B:
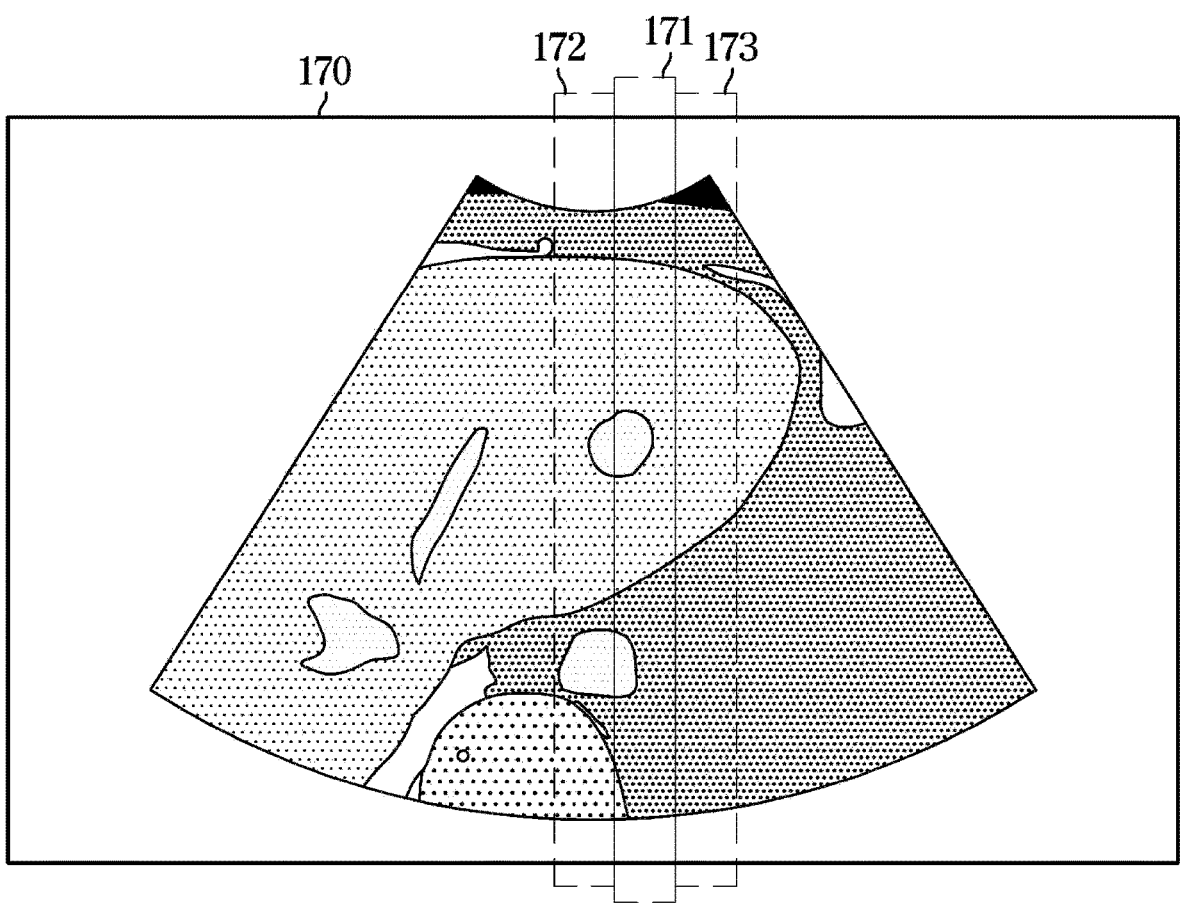

FIGS. 16A and 16B are views for describing an image correction process of an ultrasonic apparatus according to exemplary embodiments of the disclosure.

Referring to FIG. 16A, when the error occurs in a specific transmission channel (one of the transmission channels 110-1, 110-2, . . . , and 110-N of the transmitter 110, e.g., the transmission channel 2 110-2), the transmission channel 110-2 is broken, and thus the reception channel 130-2 corresponding to the broken transmission channel 110-2 may not receive the reception signal and may not obtain the ultrasonic image data.

According to the embodiment of the disclosure, when the error occurs in the specific transmission channel 110-2 of the transmitter 110, the controller 150 may stop the operation of the transmission channel 110-2 before the transmission channel 110-2 is broken. Accordingly, the reception channel 130-2 corresponding to the transmission channel 110-2 may not receive the reception signal and thus fail to obtain the ultrasonic image data.

Since the reception channel 130-2 of the channel 101-2 including the erroneous transmission channel 110-2 fails to obtain the ultrasonic image data, the dark line defect may occur in an ultrasonic image portion 171 corresponding to the erroneous reception channel 130-2. The dark line defect may refer to a phenomenon in which no image is output in the ultrasonic image portion 171 corresponding to the reception channel 130-2 because the reception channel 130-2 does not output any data.

When the dark line defect occurs, the user may have difficulty in identifying the ultrasonic image, and the reliability of the ultrasonic apparatus 100 may be reduced.

Referring to FIG. 16B, it can be seen that an image of the ultrasonic image is corrected according to the embodiment of the disclosure.

That is, the reception channel 130-2 corresponding to the transmission channel 110-2 in which the operation is stopped obtains the ultrasonic image data based on the reception signals received by the reception channels 130-1, 130-3, and 130-6 of the nearby channels 101-1, 101-3, and 101-6 according to control of the controller 150, and thus the dark line defect may be prevented.

For example, the obtaining of the ultrasonic image data by the reception channel 130-2 of the erroneous channel 101-2 based on the reception signals received by the reception channels 130-1, 130-3, and 130-6 of the nearby channels 101-1, 101-3, and 101-6 includes calculating an average value of the reception signals of the reception channels 130-1, 130-3 and 130-6 included in the nearby channels 101-1, 101-3 and 101-6 and obtaining the calculated average value as the ultrasonic image data.

That is, the ultrasonic image portion 171 corresponding to the erroneous reception channel 130-2 may be corrected on the basis of an ultrasonic image portion 172 corresponding to the reception channel 130-1 of a nearby channel 101-1 or an ultrasonic image portion 173 corresponding to the reception channel 130-3 of another nearby channel 101-3.

FIG. 17 is a flowchart illustrating a method of controlling an ultrasonic apparatus according to another embodiment.

As described above, the reception channels 130-1, 130-2, . . . , and 130-N included in the receiver 130 may receive the attenuated output transmission signal and the output reception signal, and may detect the transmission waveform information based on the attenuated transmission signal (1101).

The controller 150 may compare the transmission waveform information of one of the plurality of channels 101-1, 101-2, . . . , and 101-N (hereinafter, referred to as 'first channel', hereinafter referred to as '101-1') with the reference waveform information, and may determine whether the transmission waveform information of the first channel 101-1 is different from the reference waveform information (1102). When the transmission waveform information of the first channel 101-1 is not different from the reference waveform information, the reception channel 130-1 may receive the attenuated output transmission signal and the output reception signal, and may detect the transmission waveform information based on the attenuated transmission signal.

When the transmission waveform information of the first channel 101-1 is different from the reference waveform information, the controller 150 may stop the operation of the transmission channel 110-1 of the first channel 101-1 (1103).

The controller 150 may control the reception channel 130-1 of the first channel 101-1 so that the reception channel 130-1 of first channel 101-1 detects the ultrasonic image based on the reception signal received by the reception channel 130-2 of the second channel (one of the channels 101-1, 101-2, . . . , and 101-N, e.g., the second channel 101-2) (1104). As described above, the second channel 101-2 may be determined the channel 101-2 including the transducer element 121-2 adjacent to the transducer element 121-1 of the first channel 101-1.

The controller 150 may also display that the first channel 101-1 has the error (1105), and of course, may display that the ultrasonic apparatus 100 has the error.

According to the ultrasonic apparatus and the method of controlling the ultrasonic apparatus of exemplary embodiments, by detecting the waveforms of the transmission signals in real time using a reception channel that receives a reception signal output from the ultrasonic probe without an additional reception channel, an operation of the transmission channel having a problem may be stopped, and deformation of the ultrasonic image due to the stop of the transmission channel may be corrected.

The exemplary embodiments of the present disclosure have thus far been described with reference to the accompanying drawings. It will be obvious to people of ordinary skill in the art that the present disclosure may be practiced in other forms than the exemplary embodiments as described above without changing the technical idea or essential features of the present disclosure. The above exemplary embodiments are only by way of example, and should not be interpreted in a limited sense.

What is claimed is:

1. An ultrasonic apparatus including a plurality of channels, each comprising:
   a transmission channel configured to generate and output a transmission signal based on a synchronization signal;
   a transducer element configured to convert the transmission signal output from the transmission channel into an ultrasonic signal and output the ultrasonic signal;
   a transceiver switching circuit configured to attenuate and output the transmission signal output from the transmission channel, and to output a reception signal that returns after the ultrasonic signal is transmitted to an object and is reflected from the object; and
   a reception channel configured to receive the attenuated output transmission signal and the output reception signal, and to detect transmission waveform information based on the attenuated transmission signal,
   wherein the ultrasonic apparatus further comprising:
   a controller configured to store reference waveform information according to a transmission condition, and to compare the detected transmission waveform information with the reference waveform information.

2. The ultrasonic apparatus according to claim 1, wherein, when the detected transmission waveform information is different from the reference waveform information, the controller is configured to stop an operation of the transmission channel.

3. The ultrasonic apparatus according to claim 2, wherein the plurality of channels comprises a first channel and a second channel including a transducer element adjacent to a transducer element of the first channel, and
   wherein the controller is configured to:
      when the transmission waveform information detected in the first channel is different from the reference waveform information, stop the operation of the transmission channel of the first channel; and
      control the reception channel of the first channel such that a reception channel of the first channel obtains an ultrasonic image data based on a reception signal received by a reception channel of the second channel.

4. The ultrasonic apparatus according to claim 2, further comprising:
   a display,
   wherein, when the detected transmission waveform information is different from the reference waveform information, the controller is configured to display that there is an error in the transmission channel through the display.

5. A method of controlling an ultrasonic apparatus including a plurality of channels, the method comprising:
   generating and outputting, by a transmission channel, a transmission signal based on a synchronization signal;
   converting, by a transducer element, the transmission signal into an ultrasonic signal, and outputting, by a transceiver switching circuit, a reception signal that returns after the ultrasonic signal is transmitted to an object and is reflected from the object;
   attenuating and outputting, by the transceiver switching circuit, the transmission signal;
   receiving, by a reception channel, the attenuated output transmission signal and the output reception signal, and detecting transmission waveform information based on the attenuated transmission signal; and
   comparing, by a controller, the detected transmission waveform information with reference waveform information.

6. The method according to claim 5, further comprising:
   when the detected transmission waveform information is different from the reference waveform information, stopping, by the controller, an operation of the transmission channel.

7. The method according to claim 6, wherein the plurality of channels comprises a first channel and a second channel including a transducer element adjacent to a transducer element of the first channel, and
   the method further comprising:
   when the transmission waveform information detected in the first channel is different from the reference waveform information, stopping, by the controller, the operation of the transmission channel of the first channel; and
   controlling, by the controller, the reception channel of the first channel such that a reception channel of the first channel detects an ultrasonic image based on a reception signal received by a reception channel of the second channel.

8. The method according to claim 6, further comprising:
   when the detected transmission waveform information is different from the reference waveform information, displaying, by the controller, that there is an error in the transmission channel.

* * * * *